United States Patent
Tarca et al.

(10) Patent No.: US 12,270,814 B2
(45) Date of Patent: Apr. 8, 2025

(54) KITS AND METHODS FOR PREDICTION AND TREATMENT OF PREECLAMPSIA

(71) Applicants: Wayne State University, Detroit, MI (US); The United States of America, as Represented by the Secretary, Department of Health & Human Services, Bethesda, MD (US)

(72) Inventors: Adi L. Tarca, South Lyon, MI (US); Piya Chaemsaithong, Shatin (HK); Tinnakorn Chaiworapongsa, Grosse Pointe Park, MI (US); Sonia S. Hassan, Novi, MI (US); Roberto Romero, Grosse Pointe, MI (US)

(73) Assignees: Wayne State University, Detroit, MI (US); The United States of America, as Represented by the Secretary, Department of Health & Human Services, Bethesda, MD (US)

( * ) Notice: Subject to any disclaimer, the term of this patent is extended or adjusted under 35 U.S.C. 154(b) by 0 days.

(21) Appl. No.: 18/482,286

(22) Filed: Oct. 6, 2023

(65) Prior Publication Data

US 2024/0027470 A1 Jan. 25, 2024

Related U.S. Application Data

(63) Continuation of application No. 17/558,248, filed on Dec. 21, 2021, now Pat. No. 11,782,065, which is a continuation of application No. 15/773,978, filed as application No. PCT/US2016/060825 on Nov. 7, 2016, now Pat. No. 11,243,213.

(60) Provisional application No. 62/251,589, filed on Nov. 5, 2015.

(51) Int. Cl.
*G01N 33/53* (2006.01)
*A61K 35/16* (2015.01)
*C12Q 1/6883* (2018.01)
*G01N 33/68* (2006.01)

(52) U.S. Cl.
CPC ........... *G01N 33/689* (2013.01); *A61K 35/16* (2013.01); *C12Q 1/6883* (2013.01); *C12Q 2600/158* (2013.01); *C12Y 304/24007* (2013.01); *G01N 2333/96494* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,545,616 A | 8/1996 | Woodruff | |
| 11,243,213 B2* | 2/2022 | Tarca | G01N 33/689 |
| 11,782,065 B2* | 10/2023 | Tarca | G01N 33/689 |
| | | | 435/7.1 |
| 2005/0250156 A1 | 11/2005 | Shebuski et al. | |
| 2008/0267973 A1* | 10/2008 | Wang | A61P 37/08 |
| | | | 424/153.1 |
| 2010/0267034 A1 | 10/2010 | Lo et al. | |
| 2014/0141456 A1 | 5/2014 | Kumar et al. | |
| 2014/0154691 A1 | 6/2014 | Chapman et al. | |
| 2014/0287947 A1 | 9/2014 | Boniface et al. | |
| 2015/0004632 A1* | 1/2015 | Oxvig | G01N 33/689 |
| | | | 435/7.92 |
| 2015/0301058 A1 | 10/2015 | Schettini et al. | |
| 2018/0328937 A1 | 11/2018 | Tarca et al. | |

FOREIGN PATENT DOCUMENTS

WO WO2013188686 12/2013

OTHER PUBLICATIONS

Voller Alister, Diagnostic Horizons, Dynasciences Corportion, Published by Microbiological Associates, The Enzyme Linked Immunosorbent Assay, vol. 2, No. 1, Feb. 1978, pp. 1-7. (Year: 1978).*
Wong et al., Monoclonal antibody based ELISAs for measurement of activins in biological fluids, Journal of Immunological Methods, 165, 1993, pp. 1-10. (Year: 1993).*
Halmos et al., Circulating ficolin-2 and ficolin-3 in normal pregnancy and pre-eclampsia, Clinical and Experimental Immunology, 169, 2012, pp. 49-56. (Year: 2012).*
Przbyl et al., CD74-Downregulation of placental Macrophage-Trophoblastic Interactions in Preeclampsia, Circulation Research, vol. 119, Issue 1, Jun. 2016, pp. 55-68. (Year: 2016).*
Brou, et al., "Dysregulated biomarkers induce distict pathways in preterm birth", BJOG an International Journal of Obstetrics and Gynaecology, 2012, pp. 458-473.
Davies, et al., "Unique motifs and hydrophobic interactions shape the binding of modified DNA ligands to protein targets," PNAS USA, vol. 109, No. 49, 2012, pp. 19971-19976.

(Continued)

*Primary Examiner* — Gary Counts
(74) *Attorney, Agent, or Firm* — Lee & Hayes, P.C.

(57) ABSTRACT

Biomarkers tests which can be used to predict a positive or negative risk of preeclampsia are described. More specifically, a panel of biomarkers including MMP-7 and gpIIbIIIa, described. The test is useful to predict preeclampsia when a biological sample is obtained between the $16^{th}$ and $22^{nd}$ week of pregnancy. Prediction later in pregnancy can be achieved by a combination of Siglec-6, Activin A, ALCAM, and/or FCN2.

8 Claims, 14 Drawing Sheets

Specification includes a Sequence Listing.

(56) References Cited

OTHER PUBLICATIONS

Eide, et al., "Decidual Expression and Maternal Serum Levels of Heme Oxygenase 1 are Increased in Pre-eclampsia," Acta Obstetricia et Gynecologica, vol. 87, No. 3, 2008, pp. 272-279.

Galewska, et al., "Matrix metalloproteinases, MMP-7 and MMP-26, in plasma and serum of control and preeclamptic umbilical cord blood", European Journal of Obstetrics & Gynecology and Reproductive Biology, vol. 150, 2010, pp. 152-156.

Gandemer, et al., "Pregnancy-associated autoimmune neonatal thrombocytopenia: role of maternal HLA genotype", British Journal of Haematology, vol. 104, 1999, pp. 878-885.

Gold, et al., "Aptamer-based multiplexed proteomic technology for biomarker discovery," PLoS One, vol. 5, No. 12, 2010, 17 pages.

OA for U.S. Appl. No. 17/558,248, mailed on Jan. 25, 2023, Inventor Adi L. Tarca, Kits and Methods for Prediction and Treatment of Preeclampsia, 7 pages, Jan. 25, 2023.

O'Shaughnessy, et al., "Thrombophilic Polymorphisms in Preeclampsia: Altered Frequency of the Functional 98C>T Polymorphism of Glycoprotein IIIa," Journal of Medical Genetics, vol. 38, No. 11, 2001, pp. 775-777.

Podymow & August, "Update on the Use of Antihypertensive Drugs in Pregnancy, Hypertension," vol. 51, No. 4, 2008, pp. 960-969.

Przybl, et al., "CD74-Downregulation of Placental Macrophage-Trophoblastic Interactions in Preeclampsia," Circ. Res., vol. 119, No. 1, 2016, pp. 55-68.

Reister, et al., "Altered Protease Expression by Periarterial Trophoblast Cells in Severe Early-Onset Preeclampsia with IUGR," J. Perinat. Med., vol. 34, No. 4, 2006, pp. 272-279.

Seo, et al., "Regioselective Covalent Immobilization of Recombinant Antibody Binding Proteins A, G, and Protein L for Construction of Antibody Arrays". J. Am. Chem. Soc., vol. 135, No. 24, 2013, 19 pages.

Voller, Alister, "The Enzyme Linked Immunosorbent Assay (ELISA)," Diagnostic Horizons, Microbiological Associates, vol. 2, No. 1, 1978, 7 pages.

Wang, et al., "Innate Immune Response by Ficolin Binding in Apoptotic Placenta Is Associated with the Clinical Syndrome of Preeclampsia," Clin. Chem., vol. 53, No. 1, 2007, pp. 42-52.

Wu, et al., "Early Pregnancy Biomarkers in Pre-Eclampsia: A Systematic Review and Meta-Analysis," International Journal of Molecular Sciences, vol. 16, No. 9, 2015, pp. 23035-23056.

\* cited by examiner

FIG. 1

MRLTVLCAVCLLPGSLALPLPQEAGGMSELQWEQAQDYLKRFYLYDSETKNANSLE
AKLKEMQKFFGLPITGMLNSRVIEIMQKPRCGVPDVAEYSLFPNSPKWTSKVVTYRI
VSYTRDLPHITVDRLVSKALNMWGKEIPLHFRKVVWGTADIMIGFARGAHGDSYPFD
GPGNTLAHAFAPGTGLGGDAHFDEDERWTDGSSLGINFLYAATHELGHSLGMGHS
SDPNAVMYPTYGNGDPQNFKLSQDDIKGIQKLYGKRSNSRKK (SEQ ID NO: 1)

FIG. 2A

MARALCPLQALWLLEWVLLLLGACAAPPAWALNLDPVQLTFYAGPNGSQFGFSLDFH
KDSHGRVAIVVGAPRTLGPSQEETGGVFLCPWRAEGGQCPSLLFDLRDETRNVGS
QTLQTFKARQGLGASVVSWSDVIVACAPWQHWNVLEKTEEAEKTPVGSCFLAQPE
SGRRAEYSPCRGNTLSRIYVENDFSWDKRYCEAGFSSVVTQAGELVLGAPGGYYFL
GLLAQAPVADIFSSYRPGILLWHVSSQSLSFDSSNPEYFDGYWGYSVAVGEFDGDLN
TTEYVVGAPTWSWTLGAVEILDSYYQRLHRLRAEQMASYFGHSVAVTDVNGDGRHD
LLVGAPLYMDSRADRKLAEVGRVYLFLQPRGPHALGAPSLLLTGTQLYGRFGSAIAPL
GDLDRDGYNDIAVAAPYGGPSGRGQVLVFLGQSEGLRSRPSQVLDSPFPTGSAFGF
SLRGAVDIDDNGYPDLIVGAYGANQVAVYRAQPVVKASVQLLVQDSLNPAVKSCVLP
QTKTPVSCFNIQMCVGATGHNIPQKLSLNAELQLDRQKPRQGRRVLLLGSQQAGTTL
DLDLGGKHSPICHTTMAFLRDEADFRDKLSPIVLSLNVSLPPTEAGMAPAVVLHGDTH
VQEQTRIVLDCGEDDVCVPQLQLTASVTGSPLLGADNVLELQMDAANEGEGAYEA
ELAVHLPQGAHYMRALSNVEGFERLICNQKKENETRVVLCELGNPMKKNAQIGIAML
VSVGNLEEAGESVSFQLQIRSKNSQNPNSKIVLLDVPVRAEAQVELRGNSFPASLVVA
AEEGEREQNSLDSWGPKVEHTYELHNNGPGTVNGLHLSIHLPGQSQPSDLLYILDIQ
PQGGLQCFPQPPVNPLKVDWGLPIPSPSPIHPAHHKRDRRQIFLPEPEQPSRLQDPV
LVSCDSAPCTVVQCDLQEMARGQRAMVTVLAFLWLPSLYQRPLDQFVLQSHAWFN
VSSLPYAVPPLSLPRGEAQVWTQLLRALEERAIPIWWVLVGVLGGLLLLTILVLAMWK
VGFFKRNRHTLEEDDEEGE (SEQ ID NO: 2)

FIG. 2B

MRARPRPRPLWVTVLALGALAGVGVGGPNICTTRGVSSCQQCLAVSPMCAWCSD
EALPLGSPRCDLKENLLKDNCAPESIEFPVSEARVLEDRPLSDKGSGDSSQVTQVS
PQRIALRLRPDDSKNFSIQVRQVEDYPVDIYYLMDLSYSMKDDLWSIQNLGTKLATQ
MRKLTSNLRIGFGAFVDKPVSPYMYISPPEALENPCYDMKTTCLPMFGYKHVLTLT
DQVTRFNEEVKKQSVSRNRDAPEGGFDAIMQATVCDEKIGWRNDASHLLVFTTDA
KTHIALDGRLAGIVQPNDGQCHVGSDNHYSASTTMDYPSLGLMTEKLSQKNINLIFA
VTENVVNLYQNYSELIPGTTVGVLSMDSSNVLQLIVDAYGKIRSKVELEVRDLPEEL
SLSFNATCLNNEVIPGLKSCMGLKIGDTVSFSIEAKVRGCPQEKEKSFTIKPVGFKD
SLIVQVTFDCDCACQAQAEPNSHRCNNGNGTFECGVCRCGPGWLGSQCECSEE
DYRPSQQDECSPREGQPVCSQRGECLCGQCVCHSSDFGKITGKYCECDDFSCV
RYKGEMCSGHGQCSCGDCLCDSDWTGYYCNCTTRTDTCMSSNGLLCSGRGKCE
CGSCVCIQPGSYGDTCEKCPTCPDACTFKKECVECKKFDREPYMTENTCNRYCR
DEIESVKELKDTGKDAVNCTYKNEDDCVVRFQYYEDSSGKSILYVVEEPECPKGPD
ILVVLLSVMGAILLIGLAALLIWKLLITIHDRKEFAKFEEERARAKWDTANNPLYKEATS
TFTNITYRGT (SEQ ID NO: 3)

FIG. 3

MLPLLLPLLWAGALAQERRFQLEGPESLTVQEGLCVLVPCRLPTTLPASYYGYGYWF
LEGADVPVATNDPDEEVQEETRGRFHLLWDPRRKNCSLSIRDARRRDNAAYFFRLKS
KWMKYGYTSSKLSVRVMALTHRPNISIPGTLESGHPSNLTCSVPWVCEQGTPPIFSW
MSAAPTSLGPRTTQSSVLTITPRPQDHSTNLTCQVTFPGAGVTMERTIQLNVSYAPQK
VAISIFQGNSAAFKILQNTSSLPVLEGQALRLLCDADGNPPAHLSWFQGFPALNATPIS
NTGVLELPQVGSAEEGDFTCRAQHPLGSLQISLSLFVHWSSAPVPDRHSFRPPC
(SEQ ID NO: 4)

FIG. 4

MPLLWLRGFLLASCWIIVRSSPTPGSEGHSAAPDCPSCALAALPKDVPNSQPEMVEAVK
KHILNMLHLKKRPDVTQPVPKAALLNAIRKLHVGKVGENGYVEIEDDIGRRAEMNELMEQ
TSEIITFAESGTARKTLHFEISKEGSDLSVVERAEVWLFLKVPKANRTRTKVTIRLFQQQK
HPQGSLDTGEEAEEVGLKGERSELLLSEKVVDARKSTWHVFPVSSSIQRLLDQGKSSLD
VRIACEQCQESGASLVLLGKKKKKEEEGEGKKKGGGEGGAGADEEKEQSHRPFLMLQA
RQSEDHPHRRRRRGLECDGKVNICCKKQFFVSFKDIGWNDWIIAPSGYHANYCEGECP
SHIAGTSGSSLSFHSTVINHYRMRGHSPFANLKSCCVPTKLRPMSMLYYDDGQNIIKKDI
QNMIVEECGCS (SEQ ID NO: 5)

FIG. 5

MESKGASSCRLLFCLLISATVFRPGLGWYTVNSAYGDTIIIPCRLDVPQNLMFGKWKYEK
PDGSPVFIAFRSSTKKSVQYDDVPEYKDRLNLSENYTLSISNARISDEKRFVCMLVTEDN
VFEAPTIVKVFSK (SEQ ID NO: 6)

FIG. 6

MELDRAVGVLGAATLLLSFLGMAWALQAADTCPEVKMVGLEGSDKLTILRGCPGLPGAPG
DKGEAGTNGKRGERGPPGPPGKAGPPGPNGAPGEPQPCLTGPRTCKDLLDRGHFLSG
WHTIYLPDCRPLTVLCDMDTGGGWTVFQRRVDGSVDFYRDWATYKQGFGSRLGEFWL
GNDNIHALTAQGTSELRVDLVDFEDNYQFAKYRSFKVADEAEKYNLVLGAFVEGSAGDSLT
FHNNQSFSTKDQDNDLNTGNCAVMFQGAWWYKNCHVSNLNGRYLRGTHGSFANGINW
KSGKGYNYSYKVSEMKVRPA (SEQ ID NO: 7)

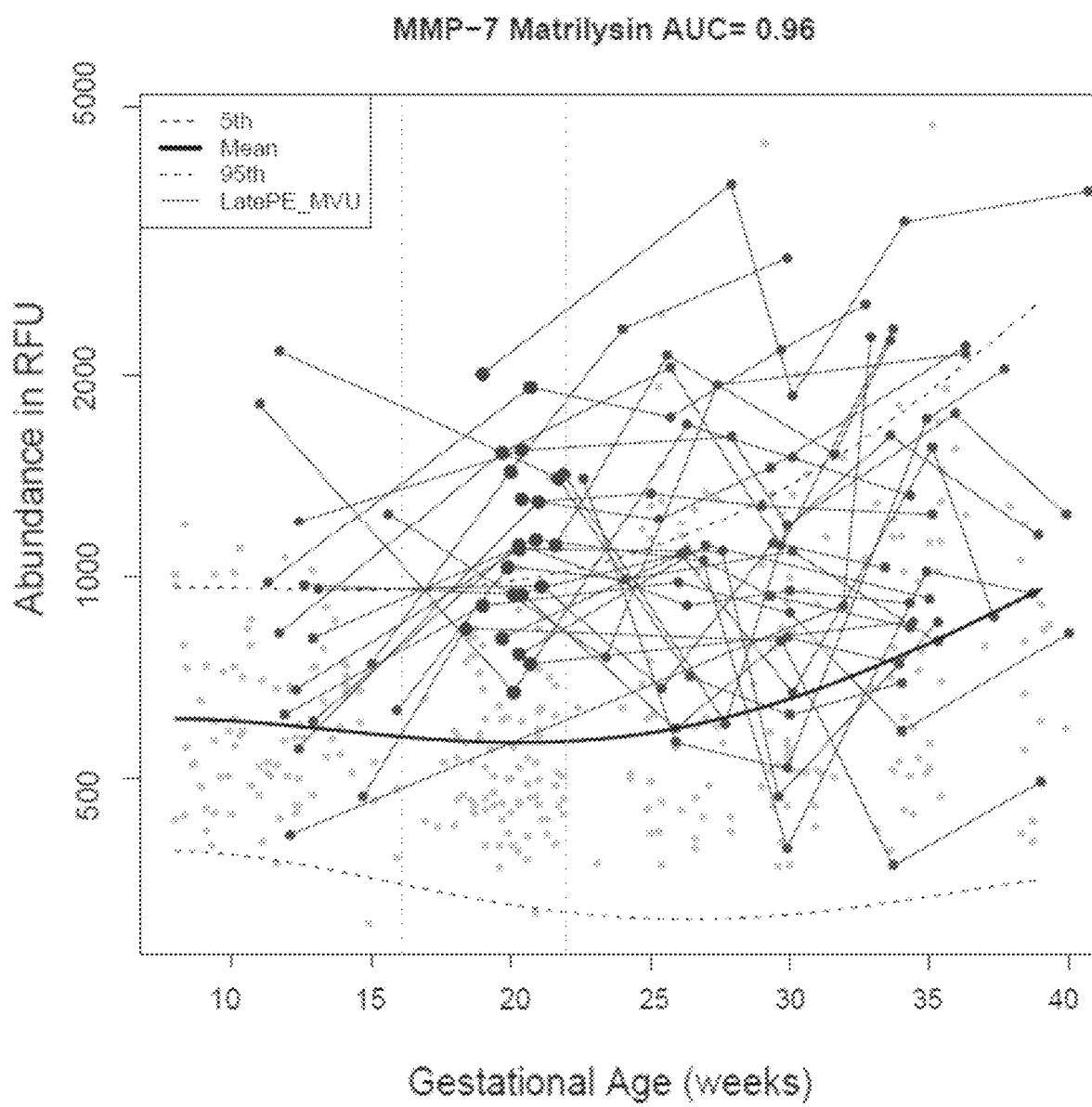

KITS AND METHODS FOR PREDICTION AND TREATMENT OF PREECLAMPSIA

CROSS-REFERENCE TO RELATED APPLICATION

This application is a continuation of U.S. patent application Ser. No. 17/558,248, filed Dec. 21, 2021, which issue d as U.S. Pat. No. 11,782,065 on Oct. 10, 2023; which is a continuation of U.S. patent application Ser. No. 15/773,978, filed May 4, 2018, which issued as U.S. Pat. No. 11,243,213 on Feb. 8, 2022; which is the U.S. National Phase of International Patent Application No. PCT/US2016/060825, which was filed on Nov. 7, 2016; and which claims priority to and the benefit of the earlier filing date of U.S. Provisional Patent Application No. 62/251,589 filed on Nov. 5, 2015. Each of these earlier filed applications is incorporated herein by reference in its entirety as if fully set forth herein.

STATEMENT REGARDING FEDERALLY SPONSORED RESEARCH

This invention was made with government support under grant NICHD grant HSN275201300006C awarded by the National Institute of Child Health and Human Development. The government has certain rights in the invention.

REFERENCE TO SEQUENCE LISTING

The nucleic acid and/or amino acid sequences described herein are shown using standard letter abbreviations, as defined in 37 C.F.R. § 1.822. A computer readable XML file, entitled "W063-0042USC2_ST26.xml" created on or about Oct. 6, 2023, with a file size of 12,288 bytes, contains the Sequence Listing for this application and is hereby incorporated by reference in its entirety.

FIELD OF THE DISCLOSURE

The present disclosure provides kits and methods for the early prediction of preeclampsia. More specifically, the kits and methods can utilize measurement of the levels of six markers, including Matrilysin (MMP-7), Integrin alpha-IIb: beta-3 complex (gpIIbIIIa), Sialic acid-binding Ig-like lectin 6 (Siglec-6), Activin A, ALCAM, and/or Ficolin-2 (FCN2).

BACKGROUND OF THE DISCLOSURE

Preeclampsia is a syndrome defined by pregnancy-induced hypertension and proteinuria, which can lead to eclampsia (convulsions), and other serious maternal and/or fetal complications. Preeclampsia originates in early gestation from the failure of implantation mechanisms and/or placental development, and is thus closely related to complications of pregnancy in early gestation such as implantation failure, and threatened and spontaneous miscarriage, Preeclampsia affects 5-7% of pregnant women (8,370,000 pregnant women worldwide per year) and is a major cause of maternal and perinatal mortality. Furthermore, women with preeclampsia have an 8-fold higher risk of cardiovascular death later in their life, and offspring born from pregnancies affected by preeclampsia have an increased risk of metabolic and cardiovascular disease and mortality later in life.

The present diagnostic criteria for preeclampsia set by the United States National High Blood Pressure Education Program Working Group on High Blood Pressure in Pregnancy include new-onset hypertension coupled with proteinuria that develops after 20 weeks of gestation in women with previously normal blood pressures. These criteria further define preeclampsia as systolic or diastolic blood pressures of $\geq 140$ and/or $\geq 90$ mmHg, respectively, measured at two or more different time points, at least 4 hours (h) but not more than 1 week apart, as well as proteinuria of $\geq 300$ mg protein in a 24 h urine sample, or two random urine specimens obtained at least 4 h but not more than 1 week apart containing $\geq 1+$ protein on a dipstick. Another sign of preeclampsia is maternal vascular underperfusion (MVU), which is a pathologic state of the placenta wherein maternal blood flow to the placenta is decreased.

Based on the timing of the clinical manifestation, preeclampsia has been historically classified into different subforms, such as "term" ($\geq 37$ weeks) and "preterm" ($< 37$ weeks) or by using an alternative terminology "late-onset" and "early-onset" preeclampsia. Preeclampsia that develops during 34 weeks of gestational age or earlier can be referred to as early-onset preeclampsia. Late-onset preeclampsia can be defined as preeclampsia that develops after 34 weeks of gestational age, and it is important to note that preeclampsia may occur intrapartum or postpartum. Thus, monitoring and evaluating the symptoms of preeclampsia should be continued during the postpartum period.

SUMMARY OF THE DISCLOSURE

The present disclosure provides kits and method that allow for the prediction of preeclampsia. The kits and methods may also allow the prediction of closely related complications of pregnancy in early gestation such as implantation failure, and threatened and spontaneous miscarriage.

The current disclosure provides that six markers that can be found in maternal plasma can be used to predict the onset of preeclampsia. These preeclampsia markers include: Matrilysin (MMP-7), Integrin alpha-IIb: beta-3 complex (gpIIbIIIa), Sialic acid-binding Ig-like lectin 6 (Siglec-6), Activin A, ALCAM, and/or Ficolin-2 (FCN2).

In particular embodiments, the kits and methods are used for assessing the presence or risk of preeclampsia in a female to determine the need for a treatment regimen including: determining levels of one or more preeclampsia markers including; MMP-7, gpIIbIIIa, Siglec-6, Activin A, ALCAM, and/or FCN2 in a biological sample obtained from the female; generating a dataset based on the determined levels; assessing the presence or risk of developing preeclampsia in the female based on the dataset; and, in particular embodiments, determining a treatment regimen based on the assessed presence or risk.

In particular embodiments, the therapeutic intervention prevents, reduces, or delays symptoms of preeclampsia before the symptoms manifest in the female and/or fetus.

In particular embodiments kits for assessing the presence or risk of preeclampsia in a female to determine the need for a treatment regimen include: detection mechanisms for determining levels of one or more of MMP-7, gpIIbIIIa, Siglec-6, Activin A, ALCAM, and/or FCN2 in a biological sample obtained from the female; instructions how to (i) generate a dataset based on the determined levels; (ii) assess the presence or risk of developing preeclampsia in the female based on the dataset; and (iii) determine a treatment regimen based on the assessed presence or risk.

In particular embodiments, the kit includes detection mechanisms for at least 1, 2, 3, 4, 5, or 6 biomarkers. In particular embodiments, the kit includes detection mechanisms for all biomarkers described above.

BRIEF DESCRIPTION OF THE DRAWINGS

FIG. 1. An exemplary sequence of Matrilysin (MMP-7, SEQ ID NO: 1).

FIGS. 2A-2B. An exemplary sequence of Integrin alpha-IIB (gpIIb, FIG. 2A, SEQ ID NO: 2) and an exemplary sequence of Integrin beta-3 (gpIIIa, FIG. 2B, SEQ ID NO: 3).

FIG. 3. An exemplary sequence of Sialic acid-binding Ig-like lectin 6 (Siglec-6, SEQ ID NO: 4).

FIG. 4. An exemplary sequence of Activin A (SEQ ID NO: 5).

FIG. 5. An exemplary sequence of ALCAM (SEQ ID NO: 6).

FIG. 6. An exemplary sequence of Ficolin-2 (FCN2, SEQ ID NO: 7).

FIGS. 7A-7C. Receiver operating characteristic (ROC) curves for MMP-7 in patients with late preeclampsia (PE) with and without maternal vascular underperfusion (MVU) (FIG. 7A). Longitudinal profiles of maternal plasma MMP-7 (FIG. 7B) in patients with late PE with MVU (gray dots). The best interval for the discrimination between late PE MVU (dark gray dots) and controls is 16.1-22 weeks of gestation. Receiver operating characteristic (ROC) curves for MMP-7 in patients with MVU (FIG. 7C).

DETAILED DESCRIPTION

Figure 7A:
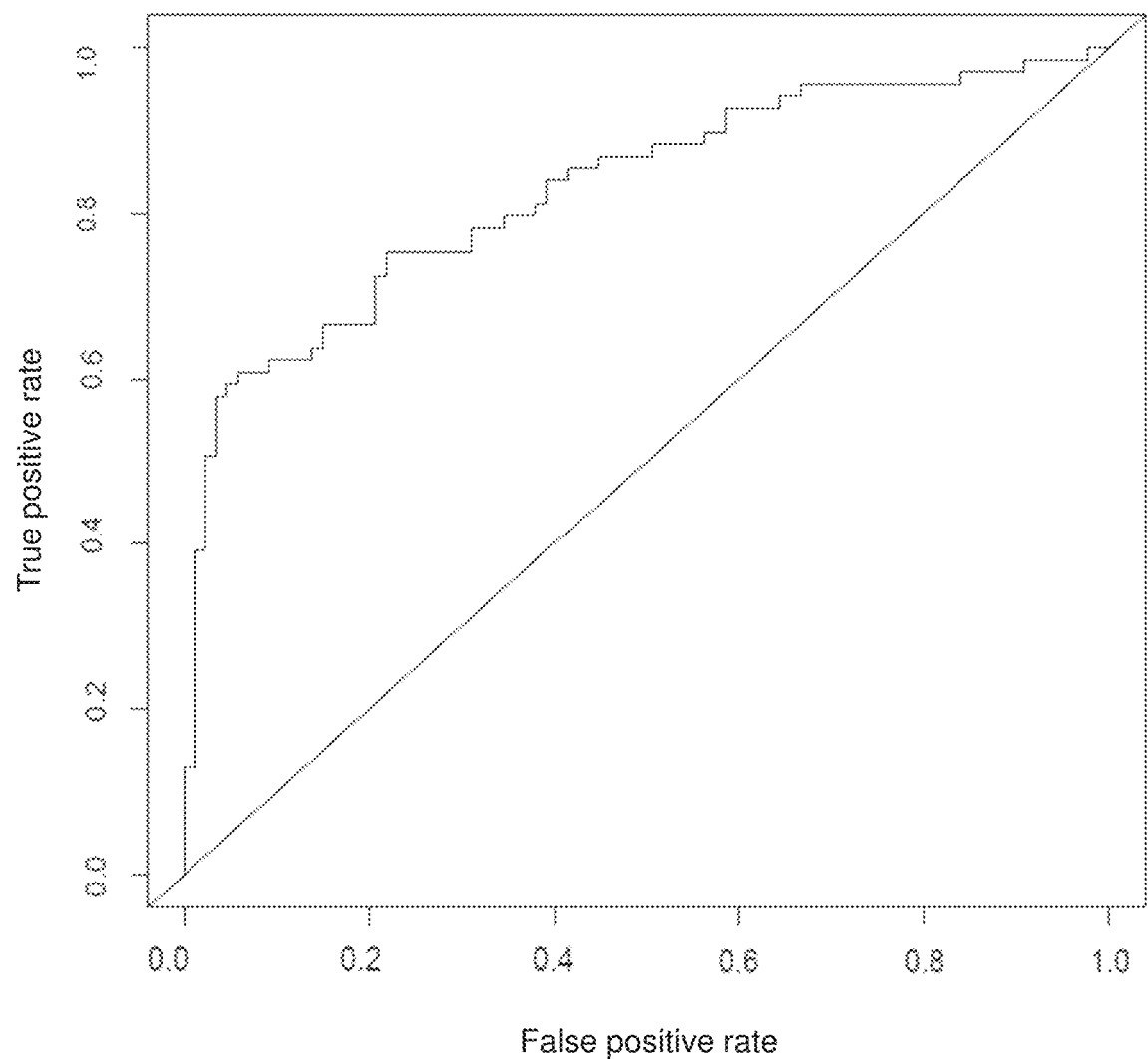

The present disclosure provides kits and methods to predict the onset of preeclampsia.

The disclosure provides that six markers in maternal plasma can be measured to predict the onset of preeclampsia. These markers include:

| Symbol | Name | UniProt ID | Outcome Predicted | GA (weeks) | AUC |
|---|---|---|---|---|---|
| MMP-7 | Matrilysin | P09237 | Early Preeclampsia | 16-22 | 0.89 |
| gpIIbIIIa | Integrin alpha-IIb: beta-3 complex | P08514/ P05106 | Early Preeclampsia | 16-22 | 0.84 |
| Siglec-6 | Sialic acid-binding Ig-like lectin 6 | O43699 | Early Preeclampsia | 22-28 | 0.91 |

-continued

| Symbol | Name | UniProt ID | Outcome Predicted | GA (weeks) | AUC |
|---|---|---|---|---|---|
| Activin A | Inhibin beta A chain | P08476 | Early Preeclampsia | 22-28 | 0.90 |
| ALCAM | CD166 antigen | Q13740 | Early Preeclampsia | 28-32 | 0.94 |
| Siglec-6 | Sialic acid-binding Ig-like lectin 6 | O43699 | Early Preeclampsia | 28-32 | 0.93 |
| FCN2 | Ficolin-2 | Q15485 | Early Preeclampsia | 28-32 | 0.92 |
| MMP-7 | Matrilysin | P09237 | Late Preeclampsia | 16-22 | 0.83 |
| Siglec-6 | Sialic acid-binding Ig-like lectin 6 | O43699 | Early Preeclampsia with MVU | 22-28 | 0.97 |

The present disclosure provides kits and method that allow for the prediction or detection of preeclampsia and may also allow the prediction of closely related complications of pregnancy in early gestation including implantation failure, and threatened and spontaneous miscarriage.

In particular embodiments, the kits and methods are used for assessing the presence or risk of preeclampsia in a female to determine the need for a treatment regimen including: determining levels of one or more preeclampsia markers including: MMP-7, gpIIbIIIa, Siglec-6, Activin A, ALCAM, and/or FCN2 in a biological sample obtained from the female; generating a dataset based on the determined levels; assessing the presence or risk of developing preeclampsia in the female based on the dataset; and, in particular embodiments, determining a treatment regimen based on the assessed presence or risk.

Compared to other technologies, methods described herein can identify women at risk of preeclampsia earlier in pregnancy (e.g., before 22 weeks of gestation). The methods described herein allow for better prediction performance in the same gestational age interval. For instance, a recent review and meta-analysis (Wu et al. (2015) Int J Mol Sci 16: 23035-23056) estimated the sensitivity of known single biomarkers for prediction of preeclampsia to be 40% at a false positive rate of 10% during the second trimester of pregnancy. The biomarkers described herein in this gestational age interval (16-22 weeks) has a sensitivity of 62% for late preeclampsia and 72% for early preeclampsia. Of note, these estimates of sensitivity are obtained assessed by bootstrap analysis, in which part of the sample set is not used in any way to identify the marker and evaluate its performance. The apparent sensitivity estimates (equivalent to those reported in Wu et al. (2015) Int J Mol Sci 16: 23035-23056) are even higher.

The test can be performed based on blood samples taken at regular prenatal care visits and can be used in assessing the risk for preeclampsia and other adverse pregnancy outcomes.

In particular embodiments, up to the 6 biomarkers described above are assessed at different dilution settings to allow obtaining concentration values instead of relative fluorescence data.

In particular embodiments, the kits and methods can utilize MMP-7 and gpIIbIIIa measurements from samples taken between the 16th and 22nd week of pregnancy to predict early onset preeclampsia.

In particular embodiments, the kits and methods can utilize MMP-7 measurements from samples taken between the 16th and 22nd week of pregnancy to predict late onset preeclampsia associated with MVU.

In particular embodiments, the kits and methods can utilize MMP-7 measurements taken during the 16th and 22$^{nd}$ week of pregnancy to predict late onset preeclampsia.

In particular embodiments, the kits and methods can utilize Siglec-6 and Activin A measurements taken between the 22nd and 28th week of pregnancy to predict early onset preeclampsia.

In particular embodiments, the kits and methods can utilize Siglec-6 measurements taken between the 22nd and 28th week of pregnancy to predict early onset preeclampsia associated with MVU.

In particular embodiments, the kits and methods can utilize ALCAM, Siglec-6 and FCN2 measurements taken between the 28th and 32nd week of pregnancy to predict early onset preeclampsia.

In particular embodiments, the assaying is performed for the levels of at least or at least 1, 2, 3, 4, 5, or 6 biomarkers.

In particular embodiments, the sample is a blood sample or a serum sample. In particular embodiments the sample is another body fluid, secretion or excretion (such as cervicovaginal fluid, saliva, or urine).

In particular embodiments, the biological sample is obtained between the 16th and 22nd week of pregnancy. In particular embodiments, the biological sample is obtained between the 22nd and 28th week of pregnancy. In particular embodiments, the biological sample is obtained between the 28th and 32nd week of pregnancy In particular embodiments, protein levels of the preeclampsia markers are measured.

In particular embodiments, the preeclampsia markers can be measured using an array with wells or spots, wherein each well or spot contains a binding ligand that binds to a specific preeclampsia marker.

In particular embodiments, the kits and methods can predict preeclampsia with a specificity of at least 90%.

In particular embodiments, the treatment regimen is a therapeutic intervention.

In particular embodiments kits for assessing the presence or risk of preeclampsia in a female to determine the need for a treatment regimen include: detection mechanisms for determining levels of one or more of MMP-7, gpIIbIIIa, Siglec-6, Activin A, ALCAM, and/or FCN2 in a biological sample obtained from the female; instructions how to (i) generate a dataset based on the determined levels; (ii) assess the presence or risk of developing preeclampsia in the female based on the dataset; and (iii) determine a treatment regimen based on the assessed presence or risk.

In particular embodiments, the kit includes detection mechanisms for at least 1, 2, 3, 4, 5, or 6 biomarkers. In particular embodiments, the kit includes detection mechanisms for all biomarkers described above.

In particular embodiments, biomarker panel tests to predict preeclampsia can include measurement of MMP-7. MMP-7 (also known as uterine metalloproteinase) is a member of the matrix metalloproteinase protein family, which are calcium dependent, zinc binding endopeptidases. The function of MMP-7 includes degradation of the extracellular matrix. MMP-7 can be expressed by epithelial cells and secreted to cleave macromolecules including fibronectin, casein, proteoglycan, and certain types of collagen. In addition to endopeptidase activity, MMP-7 has been found to activate other matrix metalloproteinases, and is upregulated in certain malignant tumors. An exemplary sequence for MMP-7 (UniProt ID P09237) is GenBank accession number Z11887 (see FIG. 1, SEQ ID NO: 1).

In particular embodiments, biomarker panel tests to predict preeclampsia can include measurement of gpIIbIIIa (glycoprotein IIb/IIIa, also known as integrin αIIbβ3). GpIIbIIIa is expressed on the surface of platelets and is involved in platelet activation. Platelet activation induces a change in gpIIbIIIa that causes it to bind to fibrinogen, allowing individual platelets to connect and form a clot. GpIIbIIIa is a heterodimer of the subunits gpIIb (or integrin alpha IIb) and gpIIIa (or integrin beta 3). An exemplary sequence for gpIIb (UniProt ID P08514) is GenBank accession number M34480 (see FIG. 2A, SEQ ID NO: 2). An exemplary sequence for gpIIIa (UniProt ID P05106) is GenBank accession number J02703 (see FIG. 2B, SEQ ID NO: 3).

In particular embodiments, biomarker panel tests to predict preeclampsia can include measurement of Siglec-6 (also known as CD327, CD33L, CDW327). The Siglec (sialic acid-binding immunoglobulin-type lectin) protein family are membrane-bound proteins that bind to sialic acid. Siglec-6 is expressed on the surface of trophoblasts and upregulation of Siglec-6 in placental tissue is associated with pregnancy complications. An exemplary sequence for Siglec-6 (UniProt ID O43699) is GenBank accession number D86359 (see FIG. 3, SEQ ID NO: 4).

In particular embodiments, biomarker panel tests to predict preeclampsia can include measurement of Activin A. Activins are protein complexes that enhance follicle-stimulating hormone synthesis and secretion. Follicle-stimulating hormone is involved in ovulation in females and maturation of germ cells in both males and females. Activin A is a homodimer of two subunits of Activin Beta-A. Activin Beta-A can bind to other subunits to form heterodimers, such as Inhibin A and Activin AB. An exemplary sequence for Activin Beta-A (UniProt ID P08476) is GenBank accession number M13436 (see FIG. 4, SEQ ID NO: 5).

In particular embodiments, biomarker panel tests to predict preeclampsia can include measurement of ALCAM (also known as CD166). ALCAM is a membrane-bound member of the immunoglobulin superfamily and is involved in T cell activation. ALCAM can mediate cell-cell interactions through heterotypic interaction, by binding to CD6, or through homotypic interaction (binding to ALCAM expressed on other cells). An exemplary sequence for ALCAM (UniProt ID Q13740) is GenBank accession number AY644765 (see FIG. 5, SEQ ID NO: 6).

In particular embodiments, biomarker panel tests to predict preeclampsia can include measurement of FCN2 (also known as P35). Ficolins are secreted pattern recognition receptors, which are a component of the innate immune system that recognize molecular patterns associated with pathogens or cellular damage. Ficolin-2 binds to sugars present on the surface of bacteria and induces the complement pathway of the innate immune system, which can inhibit bacterial infection by inducing damage to the bacterial cell membrane. An exemplary sequence for FCN2 (UniProt ID Q15485) is GenBank accession number D49353 (see FIG. 6, SEQ ID NO: 7).

MMP-7, gpIIbIIIa, Siglec-6, Activin A, ALCAM, and/or FCN2 are "biomarkers" or "markers" in the context of the present disclosure. Biomarkers include the protein forms of the markers as well as associated nucleic acids, oligonucleotides, and metabolites, together with their related metabolites, mutations, isoforms, variants, polymorphisms, modifications, fragments, subunits, degradation products, elements, and other analytes or sample-derived measures. Biomarkers can also include mutated proteins, mutated nucleic acids, variations in copy numbers, and/or transcript variants. Biomarkers also encompass combinations of any one or more of the foregoing measurements, including temporal trends and differences. Particular embodiments of biomarkers include MMP-7 (SEQ ID NO: 1); gpIIbIIIa (SEQ ID NOs: 2-3); Siglec-6 (SEQ ID NO: 4); Activin A (SEQ ID NO: 5); ALCAM (SEQ ID NO: 6); and/or FCN2 (SEQ ID NO: 7).

Protein expression patterns can be evaluated using any method that provides a quantitative measure and is suitable for evaluation of multiple markers extracted from samples. Exemplary methods include: ELISA sandwich assays, mass spectrometric detection, calorimetric assays, binding to a protein array (e.g., antibody array), or fluorescent activated cell sorting (FACS). Approaches can use labeled affinity reagents (e.g., antibodies, small molecules, etc.) that recognize epitopes of one or more protein products in an ELISA, antibody array, or FACS screen.

In particular embodiments, the preeclampsia markers can be measured using immunoassay techniques. Immunoassays are laboratory procedures that utilize antibodies and/or antigens to detect a molecule. In particular embodiments, an immunoassay can be quantitative by using secondary antibodies that are coupled to a fluorescent, chemiluminescent, or colorimetric probe.

In particular embodiments, the preeclampsia markers can be detected using antibody-based techniques. In particular embodiments, MMP-7 can be detected using an anti-MMP-7 antibody. An example of a commercially available anti-MMP-7 antibody is anti-MMP-7 ab5706, available from Abcam. In particular embodiments, gpIIbIIIa can be detected using an anti-gpIIbIIIa antibody. An example of a commercially available anti-gpIIbIIIa antibody is anti-gpIIbIIIa ab662, available from Abcam. In particular embodiments, Siglec-6 can be detected using an anti-Siglec-6 antibody. An example of a commercially available anti-Siglec-6 antibody is anti-Siglec-6 antibody ab38581, available from Abcam. In particular embodiments, Activin A can be detected using an anti-Activin A antibody. An example of a commercially available anti-Activin A antibody is mouse anti-Activin A ab89387, available from Abcam. In particular embodiments, ALCAM can be detected using an anti-ALCAM antibody. An example of a commercially available anti-ALCAM antibody is anti-ALCAM ab109215, available from Abcam. In particular embodiments, FCN2 can be detected using an anti-FCN2 antibody. An example of a commercially available anti-FCN2 antibody is anti-103145, available from Abcam.

In particular embodiments, the preeclampsia markers can be measured using an aptamer based assay. Aptamers are small oligonucleotides or peptides that can bind to specific ligands. Aptamers can be used in an array wherein each spot or well of the array can be coated with a specific aptamer to bind to a specific protein.

Protein detection can include detection of full-length proteins, protein fragments, mature proteins, pre-proteins, polypeptides, isoforms, mutations, variants, post-translationally modified proteins, and variants thereof, and can be detected in any suitable manner. Levels of biomarkers can be determined at the protein level, e.g., by measuring the serum levels of proteins. Such methods are well-known in the art and include, e.g., immunoassays based on antibodies to proteins encoded by the genes, aptamers, or molecular imprints. Any biological material can be used for the detection/quantification of the protein or its activity. Alternatively, a suitable method can be selected to determine the activity of proteins. Such assays include protease assays, kinase assays, phosphatase assays, and reductase assays, among many others.

Variants of the sequences disclosed and referenced herein are also included. Variants of peptides can include those having one or more conservative amino acid substitutions. As used herein, a "conservative substitution" involves a substitution found in one of the following conservative substitutions groups: Group 1: Alanine (Ala), Glycine (Gly), Serine (Ser), Threonine (Thr); Group 2: Aspartic acid (Asp), Glutamic acid (Glu); Group 3: Asparagine (Asn), Glutamine (Gln); Group 4: Arginine (Arg), Lysine (Lys), Histidine (His); Group 5: Isoleucine (Ile), Leucine (Leu), Methionine (Met), Valine (Val); and Group 6: Phenylalanine (Phe), Tyrosine (Tyr), Tryptophan (Trp).

Additionally, amino acids can be grouped into conservative substitution groups by similar function or chemical structure or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cysteine (Cys); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) Proteins, W.H. Freeman and Company.

Variants of the protein and nucleic acid sequences disclosed or referenced herein also include sequences with at least 70% sequence identity, 80% sequence identity, 85% sequence, 90% sequence identity, 95% sequence identity, 96% sequence identity, 97% sequence identity, 98% sequence identity, or 99% sequence identity to the protein and nucleic acid sequences disclosed or referenced herein and particularly including SEQ ID NOs:1-7.

"% sequence identity" or "% identity" refers to a relationship between two or more sequences, as determined by comparing the sequences. In the art, "identity" also means the degree of sequence relatedness between proteins or nucleic acid sequences as determined by the match between strings of such sequences. "Identity" (often referred to as "similarity") can be readily calculated by known methods, including those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wisconsin). Multiple alignment of the sequences can also be performed using the Clustal method of alignment (Higgins and Sharp CABIOS, 5, 151-153 (1989)) with default parameters (GAP PENALTY=10, GAP LENGTH PENALTY=10). Relevant programs also include the GCG suite of programs (Wisconsin Package Version 9.0, Genetics Computer Group (GCG), Madison, Wisconsin); BLASTP, BLASTN, BLASTX (Altschul, et al., J. Mol. Biol. 215:403-410 (1990)); DNASTAR (DNASTAR, Inc., Madison, Wisconsin); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y.). Within the context of this disclosure it will be understood that where sequence analysis software is used for analysis, the results of the analysis are based on the "default values" of the program referenced. As used herein "default values" will mean any set of values or parameters which originally load with the software when first initialized.

Using sequence information provided by public database entries for the biomarkers described herein, expression of the biomarker can be detected and measured using techniques well-known to those of skill in the art. For example, nucleic acid sequences in the sequence databases that correspond to nucleic acids of biomarkers can be used to construct primers and probes for detecting and/or measuring biomarker nucleic acids. These probes can be used in, e.g., Northern or Southern blot hybridization analyses, ribonuclease protection assays, and/or methods that quantitatively amplify specific nucleic acid sequences. As another example, sequences from sequence databases can be used to construct primers for specifically amplifying biomarker sequences in, e.g., amplification-based detection and quantitation methods such as reverse-transcription based polymerase chain reaction (RT-PCR) and PCR. When alterations in gene expression are associated with gene amplification, nucleotide deletions, polymorphisms, post-translational modifications and/or mutations, sequence comparisons in test and reference populations can be made by comparing relative amounts of the examined DNA sequences in the test and reference populations.

A number of methods for obtaining expression data can be used singly or in combination for determining expression patterns and profiles in the context of the present disclosure. For example, DNA and RNA expression patterns can be evaluated by northern analysis, PCR, RT-PCR, quantitative real-time RT-PCR analysis with TaqMan assays, FRET detection, monitoring one or more molecular beacon, hybridization to an oligonucleotide array, hybridization to a cDNA array, hybridization to a polynucleotide array, hybridization to a liquid microarray, hybridization to a microelectric array, molecular beacons, cDNA sequencing, clone hybridization, cDNA fragment fingerprinting, serial analysis of gene expression (SAGE), subtractive hybridization, differential display and/or differential screening.

Gene expression changes can be related to epigenetic variations (e.g. DNA methylation). Epigenetic regulation mechanisms do not involve a change to the DNA sequence. Instead, epigenetic variations include covalent modification of DNA, RNA, and the proteins associated with DNA. These in turn can result in changes to the conformation of DNA and accessibility of regulators to the DNA. Such changes cannot be identified simply by gene sequencing. Janssen, et al., Particle and Fibre Toxicology, 10:22 (2013) studied methylation in placental tissue using methods published by Tabish, et al., PLoS ONE 2012, 7:e34674 and by Godderis, et al., Epigenomics 4:269-277 (2012). MS-MLPA (Methylation-specific Multiplex ligation-dependent probe amplification) can be used to study methylation status of specific genes, for example in Proctor, et al., Clin. Chem. 52:1276-1283 (2006). Materials and methods for MS-MLPA as used in published studies can be obtained from MRC-Holland, Amsterdam, The Netherlands. Additional methods are reviewed and compared in Shen, et al., Curr. Opin. Clin. Nutr. Metab. Care. 10:576-81 (2007); Gu et al., Nature Methods 7:133-138 (2010); Bock et al., Nature Biotech. 28:1106-1114 (2010); and Harris et al., Nature Biotech. 28:1097-1105 (2010).

In particular embodiments, the kits and methods to predict preeclampsia include use of an array to measure markers. A variety of solid phase arrays can also be employed to determine expression patterns. Exemplary formats include membrane or filter arrays (e.g., nitrocellulose, nylon), pin arrays, and bead arrays (e.g., in a liquid "slurry"). Essentially any solid support capable of withstanding the reagents and conditions necessary for performing the particular expression assay can be utilized. For example, functionalized glass, silicon, silicon dioxide, modified silicon, any of a variety of polymers, such as (poly)tetrafluoroethylene, (poly)vinylidenedifluoride, polystyrene, polycarbonate, or combinations thereof can all serve as the substrate for a solid phase array.

In particular embodiments, arrays can include "chips" composed, e.g., of one of the above-specified materials. Polynucleotide probes, e.g., RNA or DNA, such as cDNA, synthetic oligonucleotides, and the like, or protein-binding ligands such as antibodies, peptides, aptamers, antigen-binding fragments or derivatives thereof, that specifically interact with expression products of individual components of the candidate library are affixed to the chip in a logically ordered manner, i.e., in an array. In addition, any molecule with a specific affinity for either the sense or anti-sense sequence of the marker nucleotide sequence (depending on the design of the sample labeling), can be fixed to the array surface without loss of specific affinity for the marker and can be obtained and produced for array production, for example, proteins that specifically recognize the specific nucleic acid sequence of the marker, ribozymes, peptide nucleic acids (PNA), or other chemicals or molecules with specific affinity.

Detailed discussion of methods for linking nucleic acids and proteins to a chip substrate, are found in, e.g., U.S. Pat. Nos. 5,143,854; 6,087,112; 5,215,882; 5,707,807; 5,807,522; 5,958,342; 5,994,076; 6,004,755; 6,048,695; 6,060,240; 6,090,556; and 6,040,138.

Microarray expression may be detected by scanning the microarray with a variety of laser or CCD-based scanners, and extracting features with software packages, for example, Imagene (Biodiscovery, Hawthorne, C A), Feature Extraction Software (Agilent), Scanalyze (Eisen, M. 1999. SCANALYZE User Manual; Stanford Univ., Stanford, Calif. Ver 2.32.), or GenePix (Axon Instruments).

"Measuring" includes determining, assessing, calculating, and/or analyzing a value or set of values associated with a sample by measurement of marker (i.e., analyte) levels in the sample. "Determining" may further include comparing levels against constituent levels in a sample or set of samples from the same subject or other subject(s). The MMP-7, gpIIbIIIa, Siglec-6, Activin A, ALCAM, FCN2 and/or other biomarkers of the present disclosure can be determined by any of various conventional methods known in the art.

In particular embodiments, quantitative data obtained for the markers of interest and other dataset components can be subjected to an analytic process with chosen parameters. The parameters of the analytic process may be those disclosed herein or those derived using the guidelines described herein. The analytic process used to generate a result may be any type of process capable of providing a result useful for classifying a sample, for example, comparison of the obtained dataset with a reference dataset, a linear algorithm, a quadratic algorithm, a decision tree algorithm, or a voting algorithm. The analytic process may set a threshold for determining the probability that a sample belongs to a given class (high risk of preeclampsia or low risk of preeclampsia). The probability preferably is at least 50%, or at least 60%, or at least 70%, or at least 80%, or at least 90% or higher.

A "dataset" as used herein is a set of numerical values resulting from evaluation of a sample (or population of samples) under a desired condition. The values of the dataset can be obtained, for example, by experimentally obtaining measures from a sample and constructing a dataset from these measurements; or alternatively, by obtaining a dataset from a service provider such as a laboratory, or from a database or a server on which the dataset has been stored.

In particular embodiments, a dataset of values is determined by measuring biomarkers from a non-pregnant subject or a pregnant subject who does not have or did not subsequently develop preeclampsia. Datasets can be used by an interpretation function to derive a preeclampsia score, which can provide a quantitative measure of likelihood that a subject will develop preeclampsia.

The sensitivity of a diagnostic measure is also referred to as the true positive rate, or the recall in some fields. It denotes the proportion of positive results (development of preeclampsia) that are correctly identified as such. The specificity of a diagnostic measure is also referred to as the true negative rate. It denotes the proportion of negatives that are correctly identified as such (no development of preeclampsia).

In particular embodiments, the kits and methods disclosed herein have at least a 60% sensitivity and a 90% specificity. In particular embodiments, the kits and methods disclosed herein have at least an 85% sensitivity and a 90% specificity. In particular embodiments, the kits and methods disclosed herein preeclampsia is identified with a sensitivity of 60% or greater, 65% or greater, 70% or greater, 75% or greater, 80% or greater, 85% or greater.

A used herein, the term "change of abundance" with regard to changes in the marker levels can refer to an increase or decrease of more than 20%, more than 30%, more than 40%, more than 50%, more than 60%, more than 70%, more than 80%, more than 90%, more than 100%, more than 150%, or more than 200% compared to a reference level. In particular embodiments, "change of abundance" measures can be evaluated independently against a reference level without consideration of earlier comparisons in the same subject. In particular embodiments, "change of abundance" can refer to any statistically significant increase or decrease in a measure as compared to a control or reference population.

As used herein, "unchanged" measures are evaluated in relation to a previous comparison in the same subject and denote a failure to achieve a statistically significant change in a score towards or away from a reference level in the particular subject.

In particular embodiments, the amount of the biomarker(s) can be measured in a sample and used to derive a preeclampsia risk score, which preeclampsia risk score is then compared to a "reference level". Reference levels can include "normal", "control", or "no preeclampsia" levels or values, defined according to, e.g., discrimination limits or risk defining thresholds, in order to define cut-off points and/or abnormal values for preeclampsia. The reference level then is the level of one or more biomarkers or combined biomarker indices typically found in a subject who did not develop preeclampsia over the course of pregnancy. Other terms for "reference levels" include "index," "baseline," "standard", etc. Such normal levels can vary, based on whether a biomarker is used alone or in a formula combined with other biomarkers to output a score. Alternatively, the reference level can be a database of biomarker patterns from previously tested subjects who did not develop preeclampsia over a clinically relevant time period, such as over the course of a pregnancy.

In particular embodiments, "reference level" can refer to a standardized value for the markers which represents a level not associated with preeclampsia. The reference level can be a universal reference level which is useful across a variety of testing locations or can be a reference level specific for the testing location and specific immunoassay used to measure the preeclampsia markers. In particular embodiments, the reference levels of the preeclampsia markers and/or reference weighted score is derived from (i) an individual; (ii) a group of individuals; (iii) a subject before pregnancy; or (iv) a pregnant subject who did not develop preeclampsia over the course of their pregnancy; wherein the samples are obtained from individuals who did not develop preeclampsia. In particular embodiments, the subject whose samples are used to obtain a reference level can be different from the subject who is being tested for risk of onset of preeclampsia. In particular embodiments, the subject whose samples are used to obtain a reference level can be the same subject who is being tested for risk of onset of preeclampsia. When the reference level is based on samples collected from the same subject, reference level samples can be collected at earlier time-points, either before pregnancy or at earlier time-points during pregnancy.

In particular embodiments, measurement of preeclampsia markers can be used in a model to calculate a preeclampsia risk score. In particular embodiments, the preeclampsia risk score is calculated using a linear discriminant analysis (LDA) model. LDA is a method that can be used to classify data points into decision zones based on a linear combination of features. In particular embodiments, the decision zones can include high risk of preeclampsia onset and low risk of preeclampsia onset. In particular embodiments, LDA can use a linear combination of data from the measurements of preeclampsia markers to distinguish between decision zones. In particular embodiments, LDA can be used to calculate preeclampsia risk score (1), wherein one or more samples are taken from a subject between the 16th and 22nd week of pregnancy and the measurement of early-onset preeclampsia markers can be used as input values in the model. In particular embodiments, LDA can be used to calculate preeclampsia risk score (2), wherein one or more samples are taken from a subject between the 22nd and 28th week of pregnancy and the measurement of early-onset preeclampsia markers can be used as input values in the model. In particular embodiments, LDA can be used to calculate preeclampsia risk score (3), wherein one or more samples are taken from a subject between the 28th and 32nd week of pregnancy and the measurement of early-onset preeclampsia markers can be used as input values in the model. In particular embodiments, LDA can be used to calculate preeclampsia risk score (4), wherein one or more samples are taken from a subject between the 16th and 22nd week of pregnancy and the measurement of late-onset preeclampsia markers can be used as input values in the model. In particular embodiments, LDA can be used to calculate preeclampsia risk score (5), wherein one or more samples are taken from a subject between the 22nd and 28th week of pregnancy and the measurement of early-onset, MVU associated preeclampsia markers can be used as input values in the model. In particular embodiments, a preeclampsia score is an output value of the LDA. In particular embodiments, a preeclampsia score can be a numerical value, wherein a score above a particular threshold value indicates high risk of onset of preeclampsia and a score below a particular threshold value indicates low risk of onset of preeclampsia. In particular embodiments, an output value can be associated with positive risk, which can mean that the patient is at high risk (e.g., higher than average) of developing clinical symptoms of preeclampsia. In particular embodiments, an output score can be associated with negative risk (e.g., average or lower than average), which can mean that the patient is at low risk of developing clinical symptoms of preeclampsia.

"Interpretation functions," as used herein, can mean the transformation of a set of observed data into a meaningful determination of particular interest; e.g., an interpretation function may be a predictive model that is created by utilizing one or more statistical algorithms to transform a dataset of observed biomarker data into a meaningful determination of likelihood of preeclampsia in a subject.

"Predict" or "prediction" as used herein can mean the identification of patients who are at increased risk of developing the clinical symptoms of preeclampsia, and who are more likely than not to develop the clinical symptoms of preeclampsia if therapeutic interventions are not initiated. As indicated elsewhere, the clinical symptoms of preeclampsia include: systolic or diastolic blood pressures of ≥140 and/or ≥90 mmHg, respectively, at two or more time points, between 4 hours (h) and 1 week apart; proteinuria of ≥300 mg protein in a 24 h urine sample, or two random urine specimens obtained between 4 h and 1 week apart containing ≥1+ protein on a dipstick; and maternal vascular underperfusion (MVU).

Systems disclosed herein include kits to assay the biomarkers disclosed herein. Also disclosed herein are kits including one or more binding domains (e.g., antibodies, binding proteins, primers, aptamers, and/or probes that bind to the biomarkers described herein). In particular embodiments, kits disclosed herein include detection reagents, detectable labels or subsets thereof, and/or other reagents that can be used to detect the preeclampsia biomarkers. A safety notice can be associated with such reagents.

In particular embodiments, the kits may include instructions for using the kit in the methods disclosed herein. In particular embodiments, the kit may include instructions regarding preparation of the antibodies, binding proteins, primers and/or probes, use of the antibodies, binding proteins, primers and/or probes, proper disposal of the related waste, interpretation of results, and the like. The instructions can be in the form of printed instructions provided inside a carton containing the kit. The instructions can also be printed on the carton and/or on other portions of the kit. Instructions may be in the form of a sheet, pamphlet, brochure, CD-Rom, or computer-readable device, or can provide directions to instructions at a remote location, such as a website. The instructions may be in English and/or in any national or regional language.

In particular embodiments, the kits described herein include some or all of the necessary supplies needed to use the kit, thereby eliminating the need to locate and gather such supplies. The supplies can include pipettes, pipette tips, buffers, reagents, plates, films, tubes, thermocyclers, tube racks, gloves, sterilizing liquids, and the like.

In particular embodiments, the kits described herein include instructions for interpretation of preeclampsia risk scores and direction as to how to proceed with therapeutic interventions. In particular embodiments, a positive prediction result directs a therapeutic intervention so that the clinical development of preeclampsia is avoided, reduced, or delayed. Therapeutic interventions can include antiplatelet drugs; antihypertensive drugs; dietary supplementation with antioxidants (primarily vitamins C and E) and at least 1 g of calcium a day; rest; and exercise.

The Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

EXAMPLE 1

Objectives: 1) To identify maternal plasma proteins predictive of late preeclampsia; and 2) to determine whether stratification of patients with late preeclampsia according to placental histopathology improves the prediction performance.

Materials and Methods: Proteomics technique: The SOMAmer® (Slow Off-rate Modified Aptamers, SomaLogic Inc, Boulder, CO) binding reagents that allow the measurement of over 1,125 proteins in maternal plasma samples were used (Gold et al., PloS one 2010; 5(12): e15004; Davies et al., PNAS 2012; 109(49):19971-6; and SomaLogic.SOMAmer® Technical Notes. Proteomics profiling was performed by Somalogic Inc who commercializes the technology and all needed reagents. The patient serum sample was diluted and then incubated with the respective SOMAmer® mixes pre-immobilized onto streptavidin (SA)-coated beads. The beads were washed to remove all non-specifically associated proteins and other matrix constituents. Proteins that remained specifically bound to their cognate SOMAmer® reagents were tagged using an NHS-biotin reagent. After the labeling reaction, the beads were exposed to an anionic competitor solution that prevents non-specific interactions from reforming after they are disrupted. Essentially pure cognate-SOMAmer® complexes and unbound (free) SOMAmer® reagents are released from the SA beads using ultraviolet light that cleaves the photo-cleavable linker. The photo-cleavage eluate, which contains all SOMAmer® reagents (some bound to a biotin-labeled protein and some free), was separated from the beads and then incubated with a second streptavidin-coated bead that binds the biotin-labeled proteins and the biotin-labeled protein-SOMAmer® complexes. The free SOMAmer® reagents were then removed during subsequent washing steps. In the final elution step, protein-bound SOMAmer® reagents were released from their cognate proteins using denaturing conditions. These SOMAmer® reagents were then quantified by hybridization to custom DNA microarrays. The Cyanine-3 signal from the SOMAmer® reagent was detected on microarrays.

A case-control longitudinal study was conducted to include 90 patients with normal pregnancies (controls) and 76 patients with late preeclampsia (cases; delivery ≥34 weeks of gestation). Maternal plasma samples were collected throughout gestation [median number of samples per patient (interquartile range, IQR) controls: 2(2-5); cases: 5(4.8-6)]. The abundance of 1,125 proteins was measured using an Aptamer based proteomics technique.

Protein abundance in normal pregnancies was modeled using linear mixed effects models to estimate mean and standard deviation (SD) as a function of gestational age. Data for all samples was then expressed as Z-scores relative to the mean (log) value in normal pregnancies. Multi-marker prediction models were built using data from one of four gestational age intervals (8-16, 16.1-22, 22.1-28, 28.1-32 weeks of gestation). Receiver operating characteristic (ROC) curves were compared for top biomarkers between cases of late preeclampsia with and without maternal vascular underperfusion (MVU) lesion in the placenta.

Figure 7C:
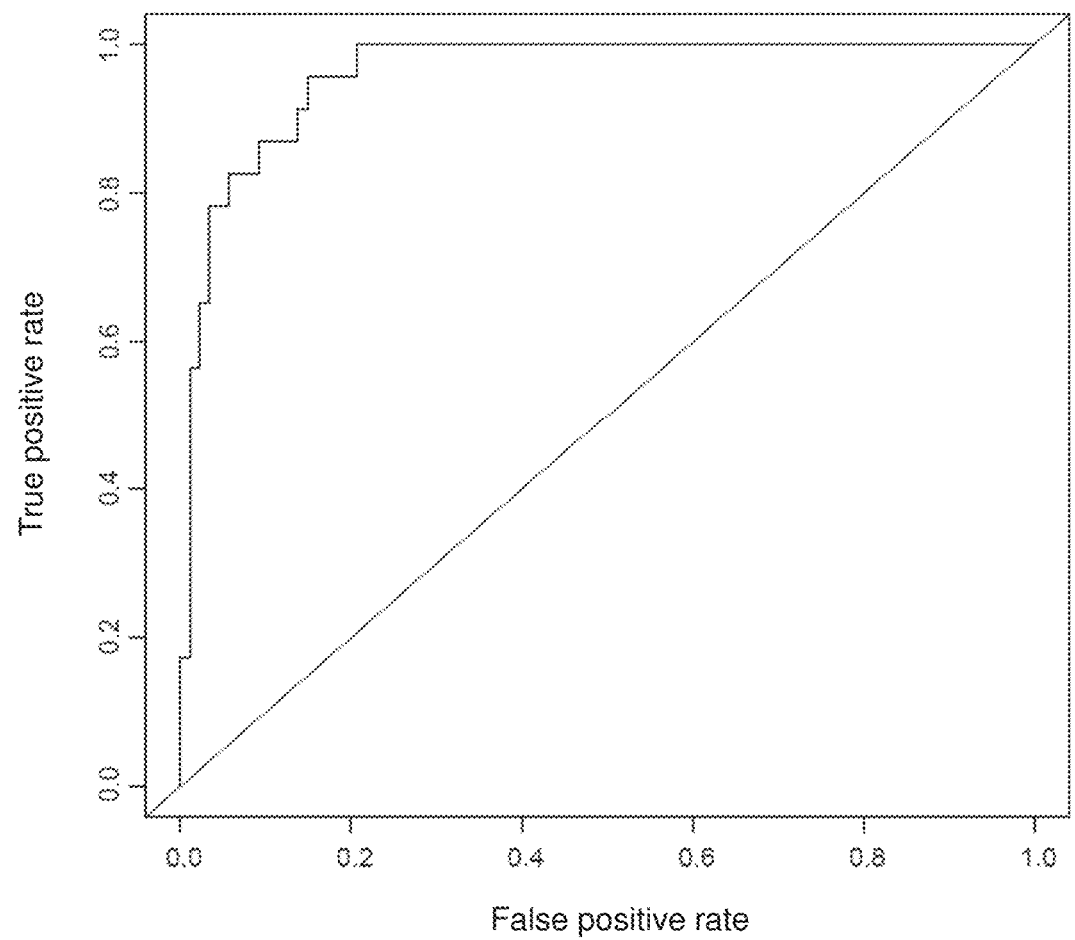

Results: 1) The highest sensitivity for predicting late preeclampsia prior to diagnosis was achieved by a Biomarker-1 (MMP-7) between 16.1-22 weeks of gestation [area under the curve (AUC)=0.83 FIG. 7A, sensitivity of 62%, at 10% false positive rate (FPR)]; 2) the mean level of this marker was higher in cases than in controls only in early (<22 weeks), but not in late gestation; and 3) disaggregation of patients based on the presence of MVU lesions in the placenta improves the predictive ability (FIG. 7B) for preeclampsia (late preeclampsia with MVU: AUC=0.96 (FIG. 7C, sensitivity=87% at 10% FPR; and late preeclampsia without MVU: AUC=0.76, sensitivity=50% at 10% FPR; p<0.0001).

Conclusions: This study reports the discovery of a novel biomarker for the prediction of late preeclampsia, which can be used between 16-22 weeks of gestation. This biomarker has a unique behavior, as differences are observed only in early but not in late gestation. Moreover, that classification of preeclampsia according to histopathologic findings improves the prediction of disease was demonstrated. This has implications for the identification of targets for intervention.

EXAMPLE 2

Objective: To identify maternal plasma proteins predictive of early preeclampsia before the onset of disease.

Materials and Methods: A discovery case-control longitudinal study was designed to include 90 patients with normal pregnancies (controls) and 34 patients with early preeclampsia (cases; delivery<34 weeks of gestation). Maternal plasma samples were collected throughout gestation [median number of samples per patient (interquartile range, IQR) controls: 2(2-5); cases: 4(3-4)]. The abundance of 1,125 proteins was measured in each sample using Aptamer proteomics based multiplex assays. A validation independent study was performed in a different experimental batch including 50 patients with normal pregnancies sampled longitudinally [median 4, IQR (4-4)] and 40 cases sampled once at the time of diagnosis.

Multi-marker prediction models were built using data from one of four gestational age intervals (8-16,16.1-22, 22.1-28, and 28.1-32 weeks of gestation), and performance was estimated using 50 bootstrap trials. In each trial, a training set of women (both cases and controls) was selected with replacement to build a disease prediction model, and performance was estimated based on data from women not included in the training set (testing set). The testing set performance was averaged over all bootstrap trials, and a final model was also trained and tested on all data to compute an apparent performance.

Figure 8A:
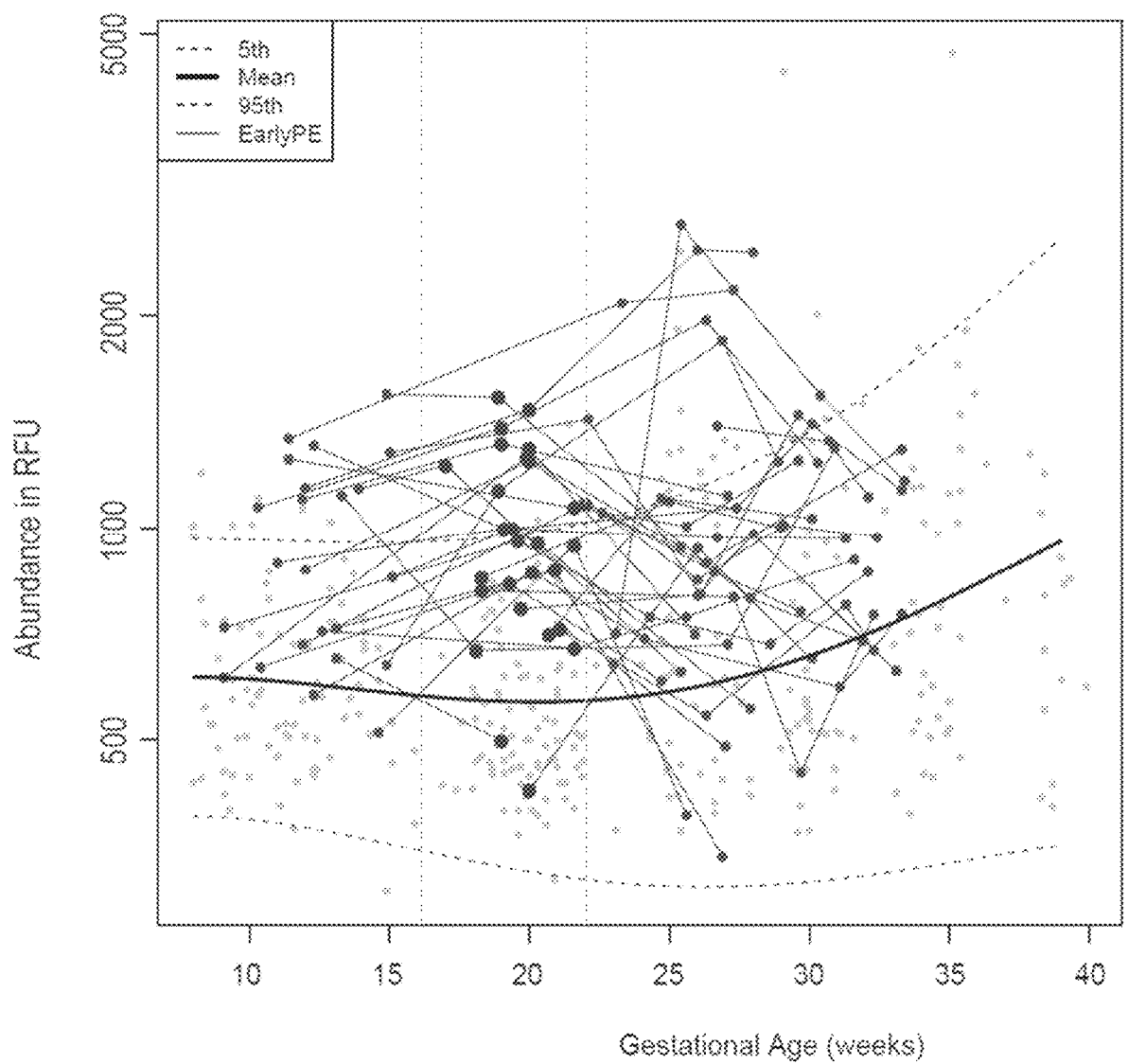
FIGS. 8A-8C. Longitudinal profiles of maternal plasma MMP-7 (FIG. 8A) and gpIIbIIIa (FIG. 8B) in patients with early preeclampsia (PE) (gray dots). In the gestational age interval 16.1-22 weeks, the discrimination between early PE (dark gray dots) and controls (light gray dots) was best for these two markers. Receiver operating characteristic (ROC) curves for MMP-7 and gpIIbIIIa (FIG. 8C).
Figure 8B:
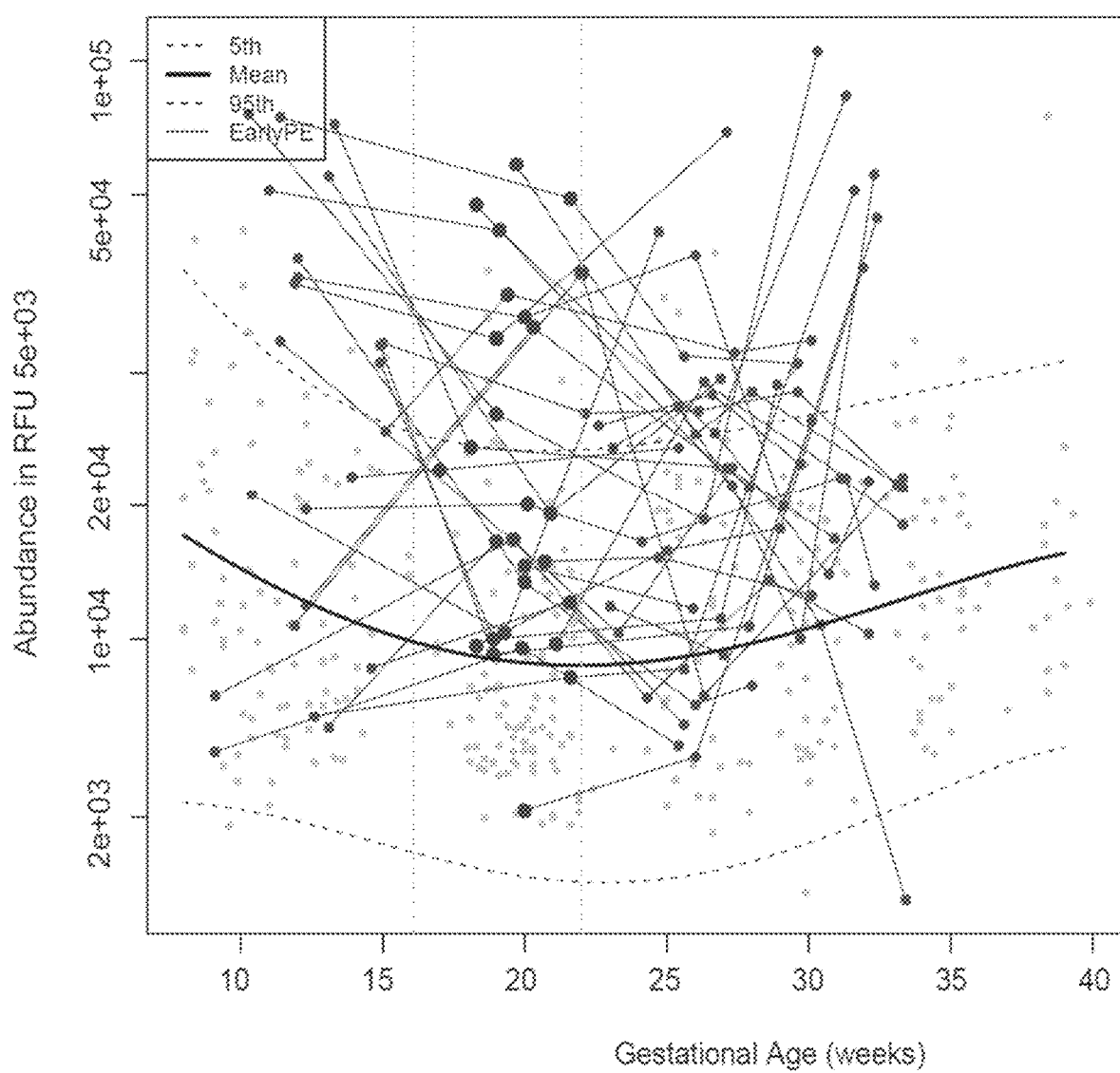
Figure 8C:
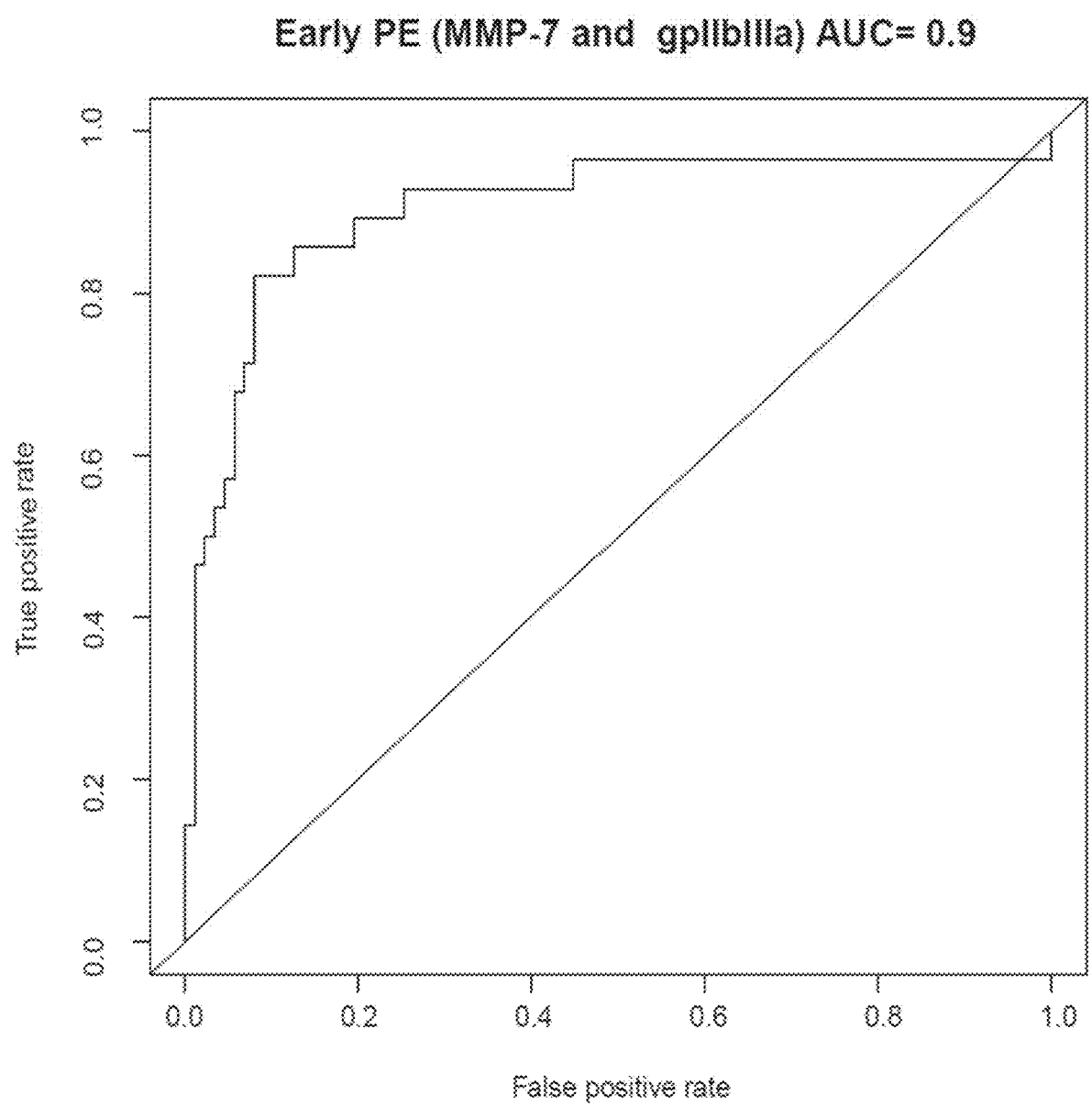

Results: 1) At 16.1-22 weeks of gestation, a combination of MMP-7 (FIG. 8A) and gpIIbIIIa (FIG. 8B) predicts the subsequent development of early preeclampsia with AUC=0.9 (FIG. 8C) and bootstrap sensitivity of 72% (82% apparent sensitivity) at 90% specificity; 2) these 2 biomarkers were selected in the best marker combination in 90% and 17% of the bootstrap trials, respectively; 3) interestingly, both proteins showed increased abundance in cases compared to controls early in pregnancy (<22 weeks) but neither later in gestation based on the discovery set (FIGS. 8A-8B) nor at the time of disease (validation set).

Figure 9A:
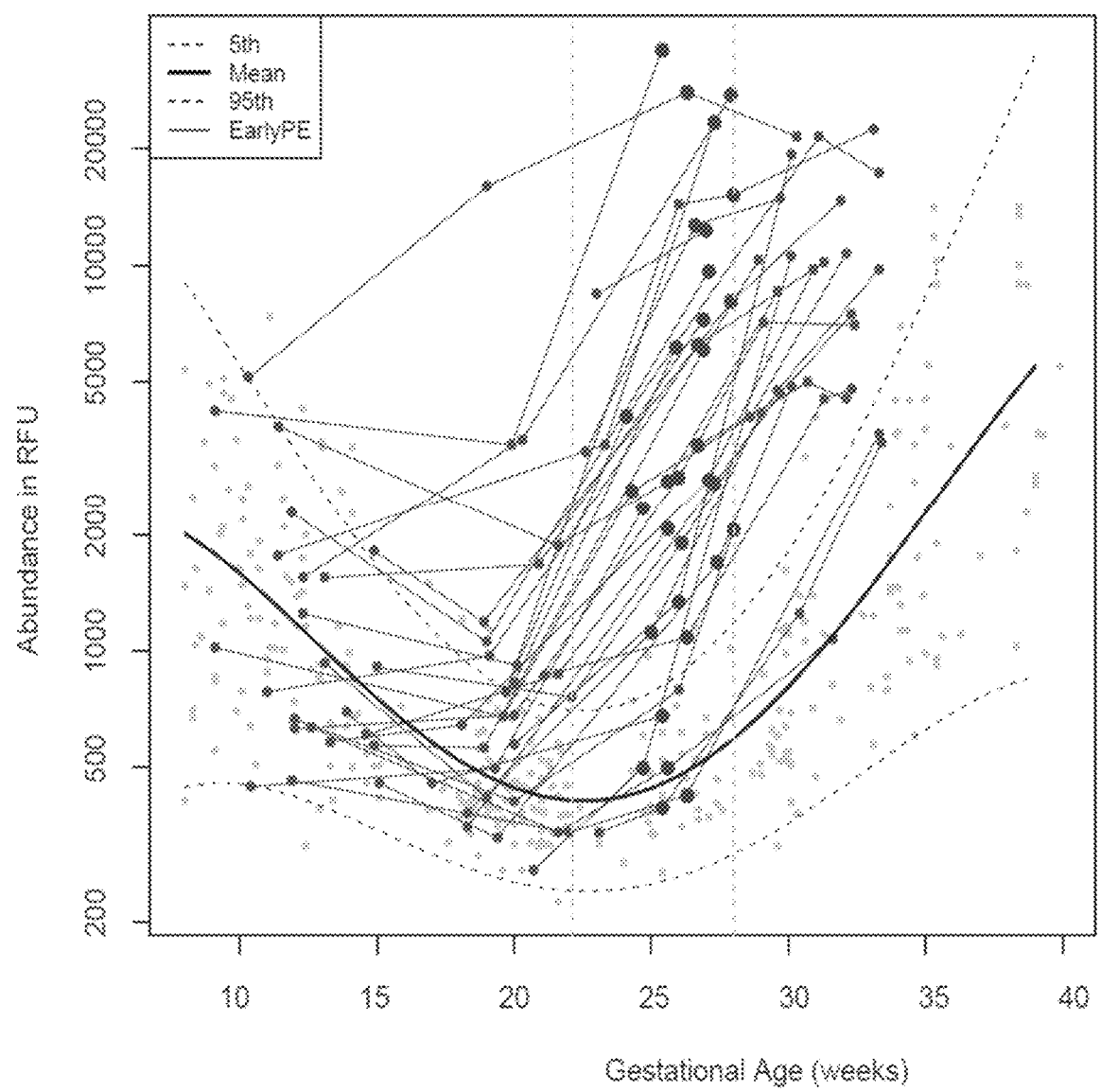
FIGS. 9A-9C. Longitudinal profiles of maternal plasma Siglec-6 (FIG. 9A) in patients with early preeclampsia (PE). Longitudinal profiles of a maternal plasma Activin A (FIG. 9B) in patients with early preeclampsia (PE). Longitudinal profiles of a maternal plasma Siglec-6 (FIG. 9C) in patients with early PE MVU. The best interval for the discrimination between early PE MVU and controls was observed in the interval 22-28 weeks of gestation.
Figure 9B:
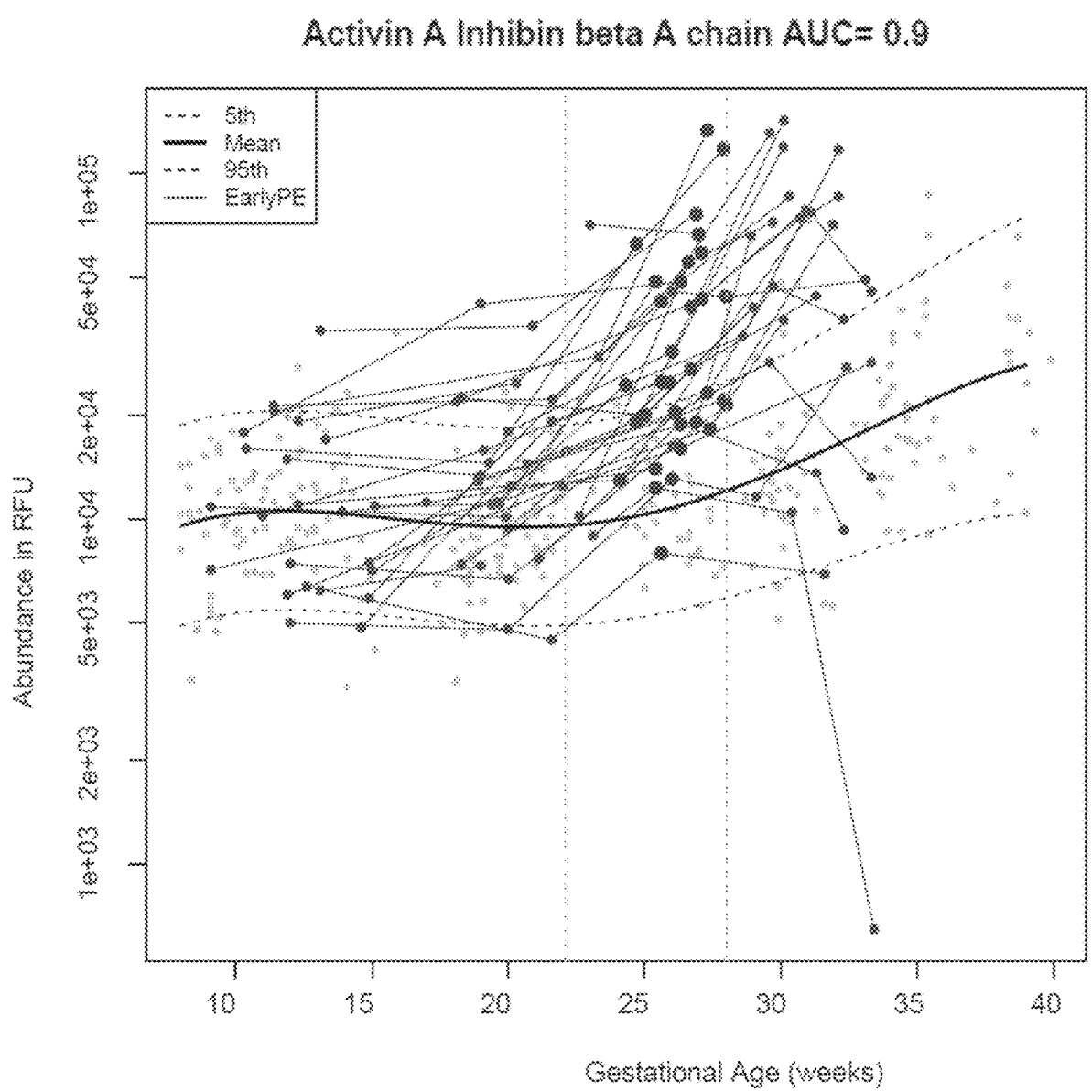
Figure 9C:
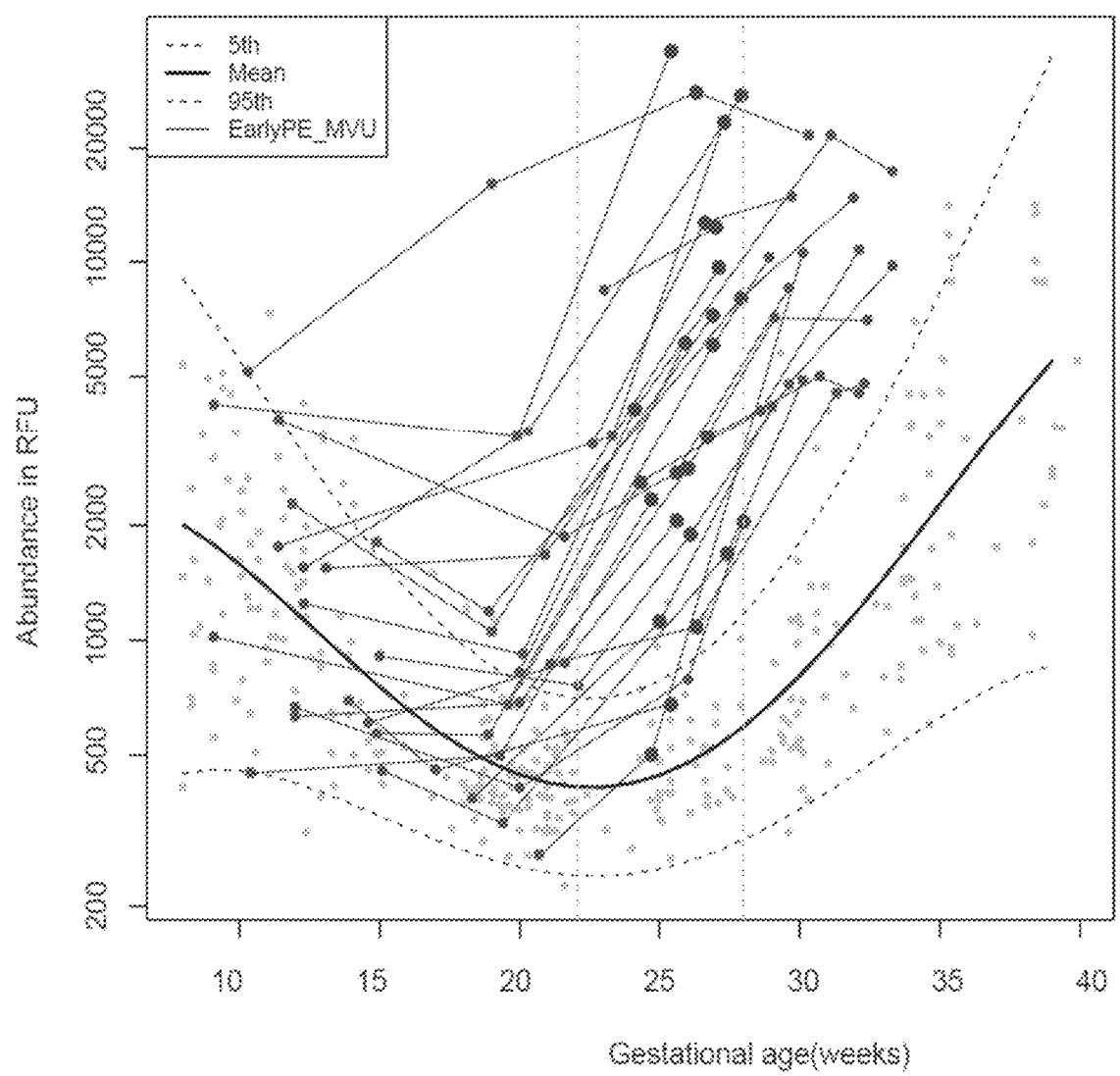

At 22-28 weeks of gestation Siglec-6 (FIG. 9A) and Activin A (FIG. 9B) predicted the subsequent development of early preeclampsia. The AUC for Siglec-6 is 0.91 and the AUC for Activin A is 0.9. Additionally, disaggregation of patients based on the presence of MVU lesions in the placenta improves the predictive ability for preeclampsia by Siglec-6 (AUC=0.97, FIG. 9C).

Figure 10A:
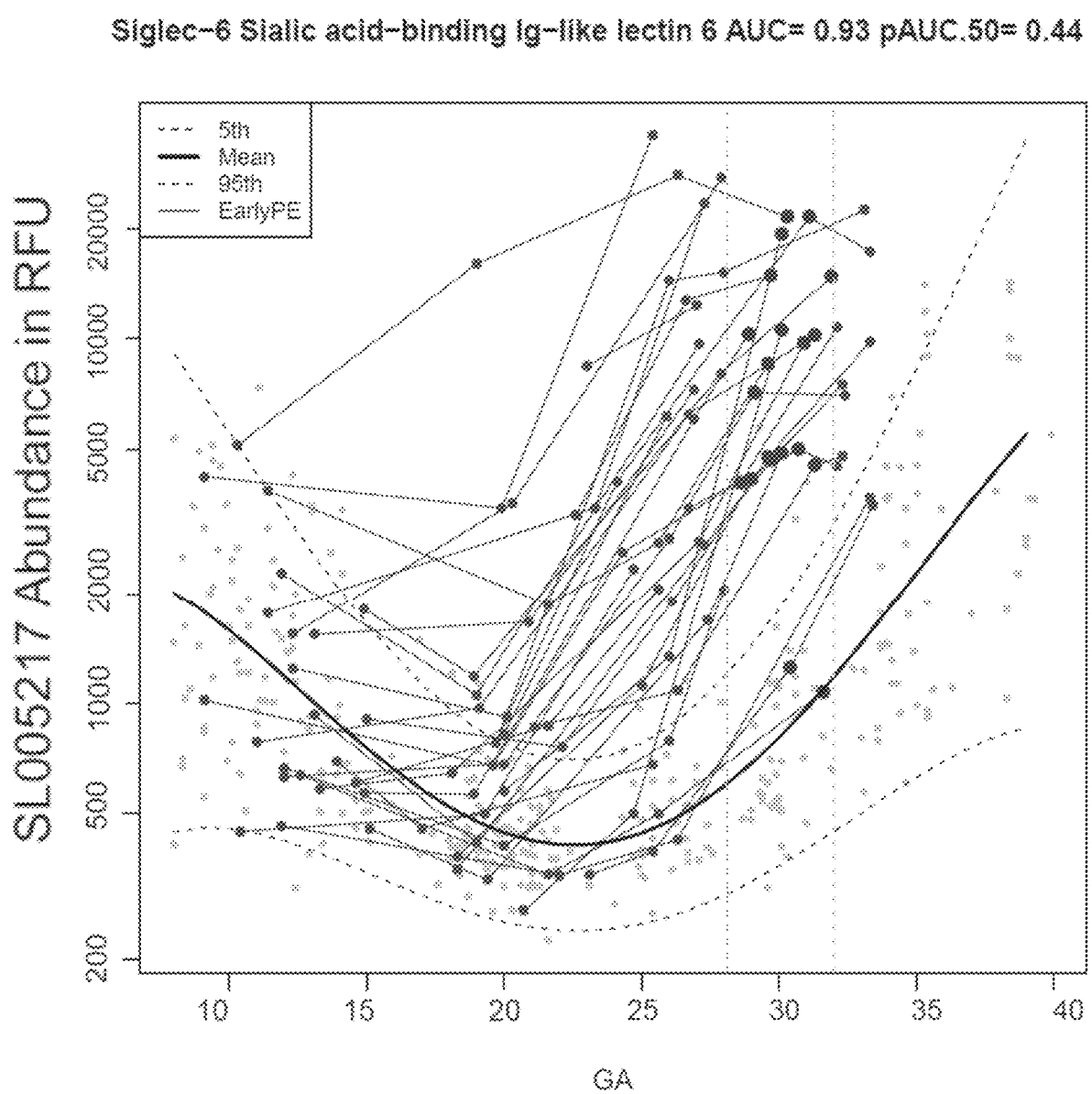
FIGS. 10A-10C. Longitudinal profiles of maternal plasma Siglec-6 (FIG. 10A) in patients with early preeclampsia (PE). Longitudinal profiles of a maternal plasma ALCAM (FIG. 10B) in patients with early preeclampsia (PE). Longitudinal profiles of a maternal plasma FCN2 (FIG. 10C) in patients with early preeclampsia (PE).
Figure 10B:
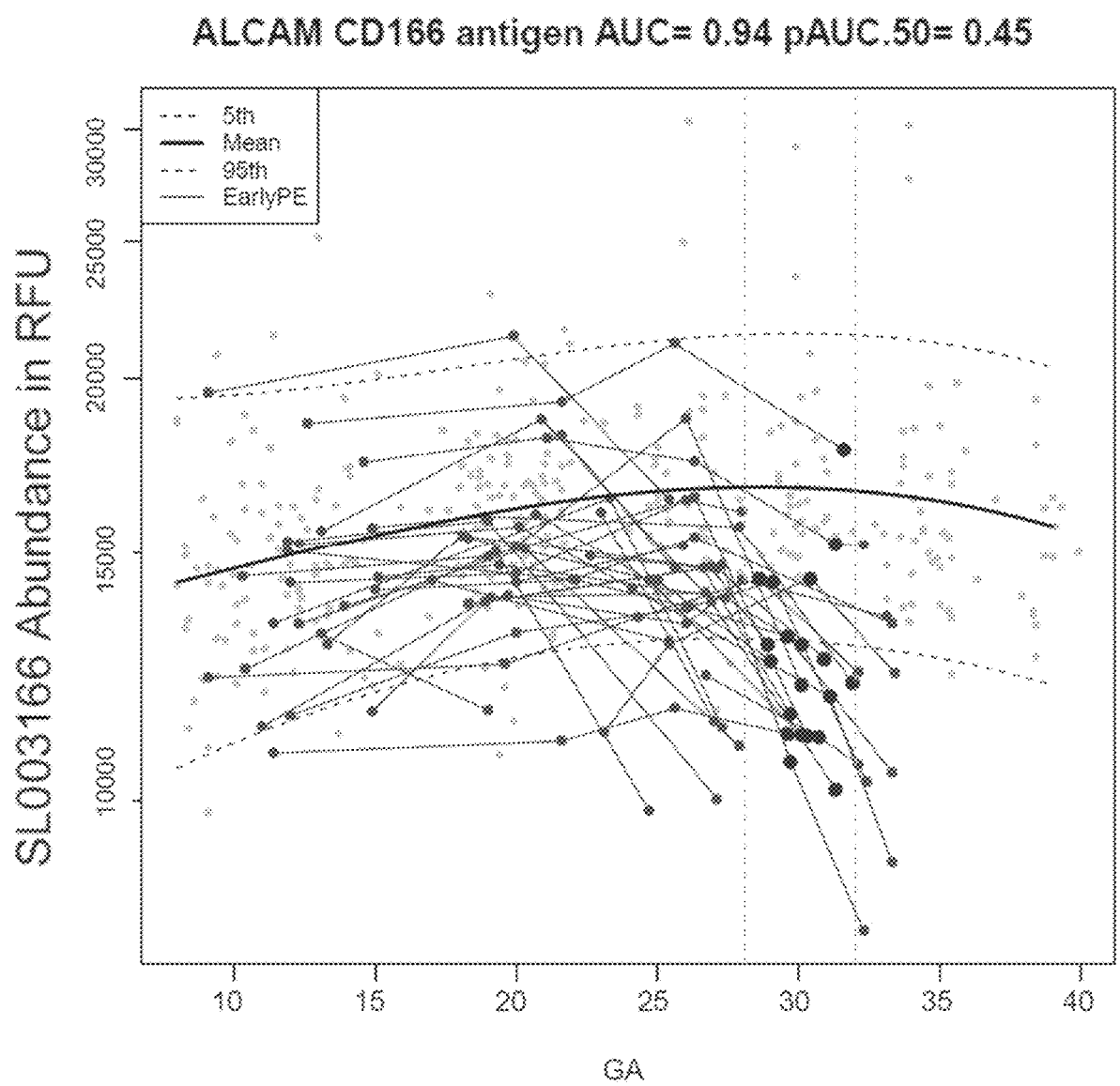
Figure 10C:
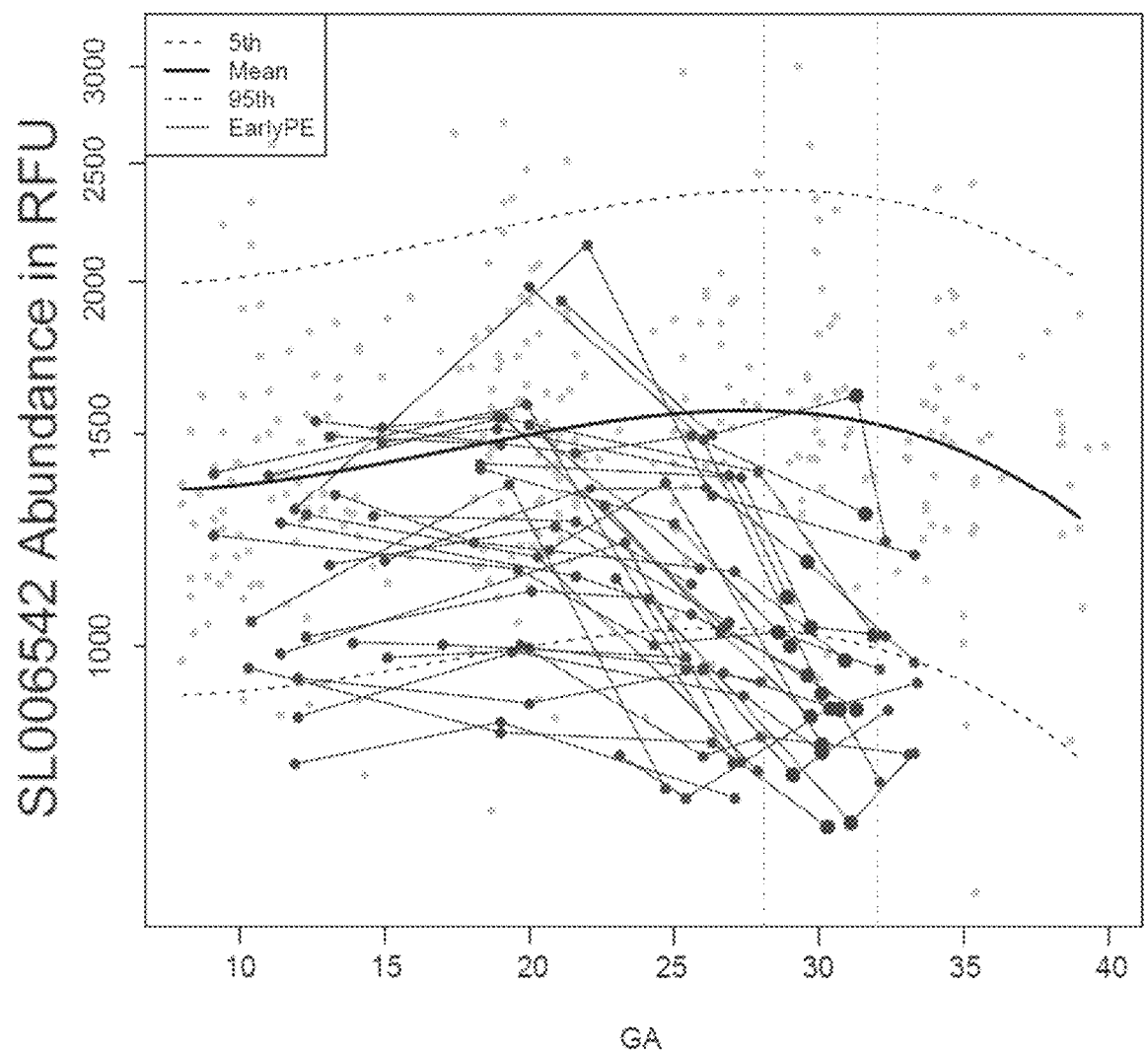

At 28-32 weeks of gestation, a combination of Siglec-6, ALCAM, and FCN2 predicts the development of early preeclampsia. The AUC for Siglec-6 in this time range is 0.93 (FIG. 10A), the AUC for ALCAM in this time range is 0.94 (FIG. 10B), and the AUC for FCN2 in this time range is 0.92 (FIG. 10O).

Conclusions: Novel biomarkers which can predict the subsequent development of early preeclampsia from 16 weeks of gestation are described. In particular, MMP-7 has a unique profile as differences in its abundance are observed in early, but not in late gestation. This is of value in the identification of patients at risk since therapeutic (e.g. prophylactic) intervention is possible.

As will be understood by one of ordinary skill in the art, each embodiment disclosed herein can comprise, consist essentially of, or consist of its particular stated element, step, ingredient or component. Thus, the terms "include" or "including" should be interpreted to recite: "comprise, consist of, or consist essentially of." As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. As used herein, a material effect would cause a statistically significant reduction in the specificity of the prediction of preeclampsia based on a sample obtained between 16-22 weeks gestational age.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the", and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually, or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

Specific embodiments disclosed herein may be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method consisting of:
obtaining a plasma or serum sample derived from a pregnant human subject in the 22$^{nd}$ to 28$^{th}$ week of gestation; and
contacting the sample with at least two binding ligands in one or more wells, wherein at least one binding ligand binds biomarker Sialic acid-binding Ig-like lectin 6 (Siglec-6) and at least one binding ligand binds biomarker Activin A.

2. The method of claim 1, wherein the contacting comprises loading samples into the one or more wells coated with Siglec-6 binding ligands; and the one or more wells coated with Activin A binding ligands.

3. A method consisting of:
   obtaining a first plasma or serum sample derived from a pregnant human subject in the $22^{nd}$ to $28^{th}$ week of gestation;
   contacting the first sample with at least two binding ligands, at least one of which binds biomarker Sialic acid-binding Ig-like lectin 6 (Siglec-6) and at least one of which binds biomarker Activin A;
   obtaining a second plasma or serum sample derived from the pregnant human subject in the $28^{th}$ to $32^{nd}$ week of gestation; and
   contacting the second sample with one or more binding ligands in one or more wells that bind a biomarker, the one or more binding ligands selected from
      at least one ligand that binds biomarker Siglec-6,
      at least one ligand that binds biomarker CD166 antigen (ALCAM), and
      at least one ligand that binds biomarker Ficolin-2 (FCN2).

4. The method of claim 3, wherein the
   one or more wells are coated with at least one of Siglec-6 binding ligands,
   ALCAM binding ligands, and
   FCN2 binding ligands.

5. A method consisting of:
   assaying a serum or plasma sample obtained from a pregnant human subject in the $22^{nd}$ to $28^{th}$ week of gestation for expression level of biomarker proteins Sialic acid-binding Ig-like lectin 6 (Siglec-6) and Activin A:
   wherein the assaying comprises loading samples into one or more wells coated with binding ligands.

6. The method of claim 5 wherein at least one of the one or more wells coated with binding ligands is coated with
   Siglec-6 binding ligands, and at least one of the one or more wells coated with binding ligands is coated with
   Activin A binding ligands.

7. A method consisting of:
   assaying a first serum or plasma sample obtained from a pregnant human subject in the $22^{nd}$ to $28^{th}$ week of gestation for expression level of biomarker proteins Sialic acid-binding Ig-like lectin 6 (Siglec-6) and Activin A;
   assaying a second serum or plasma sample obtained from the pregnant human subject in the $28^{th}$ to $32^{nd}$ week of gestation for expression level of biomarker proteins Siglec-6, CD166 antigen (ALCAM), and Ficolin-2 (FCN2);
   wherein the assaying of the second serum comprises loading the second sample into one or more wells coated with binding ligands.

8. The method of claim 7 wherein:
   the
   one or more wells are coated with binding ligands selected from: Siglec-6 binding ligands,
   ALCAM binding ligands, and
   FCN2 binding ligands.

* * * * *

SEQUENCE LISTING

```
Sequence total quantity: 7
SEQ ID NO: 1            moltype = AA  length = 267
FEATURE                 Location/Qualifiers
source                  1..267
                        mol_type = protein
                        organism = Homo sapiens
SEQUENCE: 1
MRLTVLCAVC LLPGSLALPL PQEAGGMSEL QWEQAQDYLK RFYLYDSETK NANSLEAKLK  60
EMQKFFGLPI TGMLNSRVIE IMQKPRCGVP DVAEYSLFPN SPKWTSKVVT YRIVSYTRDL 120
PHITVDRLVS KALNMWGKEI PLHFRKVVWG TADIMIGFAR GAHGDSYPFD GPGNTLAHAF 180
APGTGLGGDA HFDEDERWTD GSSLGINFLY AATHELGHSL GMGHSSDPNA VMYPTYGNGD 240
PQNFKLSQDD IKGIQKLYGK RSNSRKK                                    267

SEQ ID NO: 2            moltype = AA  length = 1039
FEATURE                 Location/Qualifiers
source                  1..1039
                        mol_type = protein
                        organism = Homo sapiens
SEQUENCE: 2
MARALCPLQA LWLLEWVLLL LGACAAPPAW ALNLDPVQLT FYAGPNGSQF GFSLDFHKDS   60
HGRVAIVVGA PRTLGPSQEE TGGVFLCPWR AEGGQCPSLL FDLRDETRNV GSQTLQTFKA  120
RQGLGASVVS WSDVIVACAP WQHWNVLEKT EEAEKTPVGS CFLAQPESGR RAEYSPCRGN  180
TLSRIYVEND FSWDKRYCEA GFSSVVTQAG ELVLGAPGGY YFLGLLAQAP VADIFSSYRP  240
GILLWHVSSQ SLSFDSSNPE YFDGYWGYSV AVGEFDGDLN TTEYVVGAPT WSWTLGAVEI  300
LDSYYQRLHR LRAEQMASYF GHSVAVTDVN GDGRHDLLVG APLYMDSRAD RKLAEVGRVY  360
LFLQPRGPHA LGAPSLLLTG TQLYGRFGSA IAPLGDLDRD GYNDIAVAAP YGGPSGRGQV  420
LVFLGQSEGL RSRPSQVLDS PFPTGSAFGF SLRGAVDIDD NGYPDLIVGA YGANQVAVYR  480
AQPVVKASVQ LLVQDSLNPA VKSCVLPQTK TPVSCFNIQM CVGATGHNIP QKLSLNAELQ  540
LDRQKPRQGR RVLLLGSQQA GTTLDLDLGG KHSPICHTTM AFLRDEADFR DKLSPIVLSL  600
NVSLPPTEAG MAPAVVLHGD THVQEQTRIV LDCGEDDVCV PQLQLTASVT GSPLLVGADN  660
VLELQMDAAN EGEGAYEGAEL AVHLPQGAHY MRALSNVEGF ERLICNQKKE NETRVVLCEL  720
GNPMKKNAQI GIAMLVSVGN LEEAGESVSF QLQIRSKNSQ NPNSKIVLLD VPVRAEAQVE  780
LRGNSFPASL VVAAEEGERE QNSLDSWGPK VEHTYELHNN GPGTVNGLHL SIHLPGQSQP  840
SDLLYILDIQ PQGGLQCFPQ PPVNPLKVDW GLPIPSPSPI HPAHHKRDRR QIFLPEPEQP  900
SRLQDPVLVS CDSAPCTVVQ CDLQEMARGQ RAMVTVLAFL WLPSLYQRPL DQFVLQSHAW  960
FNVSSLPYAV PPLSLPRGEA QVWTQLLRAL EERAIPIWWV LVGVLGGLLL LTILVLAMWK 1020
VGFFKRNRHT LEEDDEEGE                                             1039
```

```
SEQ ID NO: 3          moltype = AA  length = 788
FEATURE               Location/Qualifiers
source                1..788
                      mol_type = protein
                      organism = Homo sapiens
SEQUENCE: 3
MRARPRPRPL WVTVLALGAL AGVGVGGPNI CTTRGVSSCQ QCLAVSPMCA WCSDEALPLG   60
SPRCDLKENL LKDNCAPESI EFPVSEARVL EDRPLSDKGS GDSSQVTQVS PQRIALRLRP  120
DDSKNFSIQV RQVEDYPVDI YYLMDLSYSM KDDLWSIQNL GTKLATQMRK LTSNLRIGFG  180
AFVDKPVSPY MYISPPEALE NPCYDMKTTC LPMFGYKHVL TLTDQVTRFN EEVKKQSVSR  240
NRDAPEGGFD AIMQATVCDE KIGWRNDASH LLVFTTDAKT HIALDGRLAG IVQPNDGQCH  300
VGSDNHYSAS TTMDYPSLGL MTEKLSQKNI NLIFAVTENV VNLYQNYSEL IPGTTVGVLS  360
MDSSNVLQLI VDAYGKIRSK VELEVRDLPE ELSLSFNATC LNNEVIPGLK SCMGLKIGDT  420
VSFSIEAKVR GCPQEKEKSF TIKPVGFKDS LIVQVTFDCD CACQAQAEPN SHRCNNGNGT  480
FECGVCRCGP GWLGSQCECS EEDYRPSQQD ECSPREGQPV CSQRGECLCG QCVCHSSDFG  540
KITGKYCECD DFSCVRYKGE MCSGHGQCSC GDCLCDSDWT GYYCNCTTRT DTCMSSNGLL  600
CSGRGKCECG SCVCIQPGSY GDTCEKCPTC PDACTFKKEC VECKKFDREP YMTENTCNRY  660
CRDEIESVKE LKDTGKDAVN CTYKNEDDCV VRFQYYEDSS GKSILYVVEE PECPKGPDIL  720
VVLLSVMGAI LLIGLAALLI WKLLITIHDR KEFAKFEEER ARAKWDTANN PLYKEATSTF  780
TNITYRGT                                                          788

SEQ ID NO: 4          moltype = AA  length = 342
FEATURE               Location/Qualifiers
source                1..342
                      mol_type = protein
                      organism = Homo sapiens
SEQUENCE: 4
MLPLLLPLLW AGALAQERRF QLEGPESLTV QEGLCVLVPC RLPTTLPASY YGYGYWFLEG   60
ADVPVATNDP DEEVQEETRG RFHLLWDPRR KNCSLSIRDA RRRDNAAYFF RLKSKWMKYG  120
YTSSKLSVRV MALTHRPNIS IPGTLESGHP SNLTCQVTFPG AGVTMERTIQ LNVSYAPQKV  180
PRTTQSSVLT ITPRPQDHST NLTCQVTFPG AGVTMERTIQ LNVSYAPQKV AISIFQGNSA  240
AFKILQNTSS LPVLEGQALR LLCDADGNPP AHLSWFQGFP ALNATPISNT GVLELPQVGS  300
AEEGDFTCRA QHPLGSLQIS LSLFVHWSSA PVPDRHSFRP PC                    342

SEQ ID NO: 5          moltype = AA  length = 426
FEATURE               Location/Qualifiers
source                1..426
                      mol_type = protein
                      organism = Homo sapiens
SEQUENCE: 5
MPLLWLRGFL LASCWIIVRS SPTPGSEGHS AAPDCPSCAL AALPKDVPNS QPEMVEAVKK   60
HILNMLHLKK RPDVTQPVPK AALLNAIRKL HVGKVGENGY VEIEDDIGRR AEMNELMEQT  120
SEIITFAESG TARKTLHFEI SKEGSDLSVV ERAEVWLFLK VPKANRTRTK VTIRLFQQQK  180
HPQGSLDTGE EAEEVGLKGE RSELLLSEKV VDARKSTWHV FPVSSSIQRL LDQGKSSLDV  240
RIACEQCQES GASLVLLGKK KKKEEEGEGK KKGGGEGGAG ADEEKEQSHR PFLMLQARQS  300
EDHPHRRRRR GLECDGKVNI CCKKQFFVSF KDIGWNDWII APSGYHANYC EGECPSHIAG  360
TSGSSLSFHS TVINHYRMRG HSPFANLKSC CVPTKLRPMS MLYYDDGQNI IKKDIQNMIV  420
EECGCS                                                            426

SEQ ID NO: 6          moltype = AA  length = 133
FEATURE               Location/Qualifiers
source                1..133
                      mol_type = protein
                      organism = Homo sapiens
SEQUENCE: 6
MESKGASSCR LLFCLLISAT VFRPGLGWYT VNSAYGDTII IPCRLDVPQN LMFGKWKYEK   60
PDGSPVFIAF RSSTKKSVQY DDVPEYKDRL NLSENYTLSI SNARISDEKR FVCMLVTEDN  120
VFEAPTIVKV FSK                                                    133

SEQ ID NO: 7          moltype = AA  length = 313
FEATURE               Location/Qualifiers
source                1..313
                      mol_type = protein
                      organism = Homo sapiens
SEQUENCE: 7
MELDRAVGVL GAATLLLSFL GMAWALQAAD TCPEVKMVGL EGSDKLTILR GCPGLPGAPG   60
DKGEAGTNGK RGERGPPGPP GKAGPPGPNG APGEPQPCLT GPRTCKDLLD RGHFLSGWHT  120
IYLPDCRPLT VLCDMDTDGG GWTVFQRRVD GSVDFYRDWA TYKQGFGSRL GEFWLGNDNI  180
HALTAQGTSE LRVDLVDFED NYQFAKYRSF KVADEAEKYN LVLGAFVEGS AGDSLTFHNN  240
QSFSTKDQDN DLNTGNCAVM FQGAWWYKNC HVSNLNGRYL RGTHGSFANG INWKSGKGYN  300
YSYKVSEMKV RPA                                                    313
```